(12) United States Patent
Zhang et al.

(10) Patent No.: US 11,110,182 B2
(45) Date of Patent: Sep. 7, 2021

(54) MULTIFUNCTIONAL RNA NANOPARTICLES AND METHODS FOR TREATING CANCER AND THERAPEUTIC RESISTANT CANCER

(71) Applicant: University of Cincinnati, Cincinnati, OH (US)

(72) Inventors: Xiaoting Zhang, Cincinnati, OH (US); Peixuan Guo, Cincinnati, OH (US)

(73) Assignees: University of Cincinnati, Cincinnati, OH (US); Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/467,690

(22) PCT Filed: Dec. 8, 2017

(86) PCT No.: PCT/US2017/065248
§ 371 (c)(1),
(2) Date: Jun. 7, 2019

(87) PCT Pub. No.: WO2018/106992
PCT Pub. Date: Jun. 14, 2018

(65) Prior Publication Data
US 2019/0351067 A1    Nov. 21, 2019

Related U.S. Application Data

(60) Provisional application No. 62/431,640, filed on Dec. 8, 2016.

(51) Int. Cl.
| | |
|---|---|
| *A61K 47/69* | (2017.01) |
| *C12N 15/113* | (2010.01) |
| *C12N 15/115* | (2010.01) |
| *A61P 35/00* | (2006.01) |
| *A61K 31/4196* | (2006.01) |
| *A61K 31/566* | (2006.01) |

(52) U.S. Cl.
CPC ...... *A61K 47/6929* (2017.08); *A61K 31/4196* (2013.01); *A61K 31/566* (2013.01); *A61P 35/00* (2018.01); *C12N 15/113* (2013.01); *C12N 15/115* (2013.01); *C12N 2310/14* (2013.01); *C12N 2310/16* (2013.01); *C12N 2310/3519* (2013.01); *C12N 2320/32* (2013.01)

(58) Field of Classification Search
None
See application file for complete search history.

(56) References Cited

U.S. PATENT DOCUMENTS

| | | |
|---|---|---|
| 2002/0164663 A1 | 11/2002 | Fuqua et al. |
| 2005/0002900 A1 | 1/2005 | Wong et al. |
| 2007/0190023 A1 | 8/2007 | Battista et al. |
| 2012/0004181 A1 | 1/2012 | Medina-Kauwe |
| 2013/0129719 A1* | 5/2013 | Giangrande ......... C12N 15/115 424/133.1 |
| 2014/0179758 A1 | 6/2014 | Guo |
| 2014/0212503 A1* | 7/2014 | Lee ..................... A61K 9/0019 424/499 |
| 2014/0296218 A1 | 10/2014 | Young et al. |

OTHER PUBLICATIONS

Cui et al. Cancer Res; 72:5625-34 (Year: 2012).*
Xiaoting Zhang, Targeting MED1 LxxLL Motifs for Tissue-Selective Treatment of Human Breast Cancer; Sep. 2012; Prepared for U.S. Army Medical Research and Materiel Command, Fort Detrick, Maryland.
International Search Report & Written Opinion for corresponding PCT/US2017/065248 dated Mar. 5, 2018.

* cited by examiner

*Primary Examiner* — Brian Whiteman
(74) *Attorney, Agent, or Firm* — Dinsmore & Shohl LLP

(57) ABSTRACT

RNA nanoparticles functionalized with a HER2-targeting RNA aptamer and at least one MED1 siRNA for targeted delivery of MED1 siRNA to human cancer cells via human epidermal growth factor receptor 2 (HER2) receptors, pharmaceutical compositions of the inventive RNA nanoparticles, and methods for treating breast, HER2-implicated cancers, and in particular therapeutic-resistant cancer such as tamoxifen-resistant breast cancer, by administering pharmaceutical compositions of the inventive RNA nanoparticles.

16 Claims, 28 Drawing Sheets
(14 of 28 Drawing Sheet(s) Filed in Color)
Specification includes a Sequence Listing.

MED1 p-HER2-siScram+Veh    p-HER2-siScram+TAM p-HER2-siMED1+Veh    p-HER2-siMED1+TAM

Ki-67

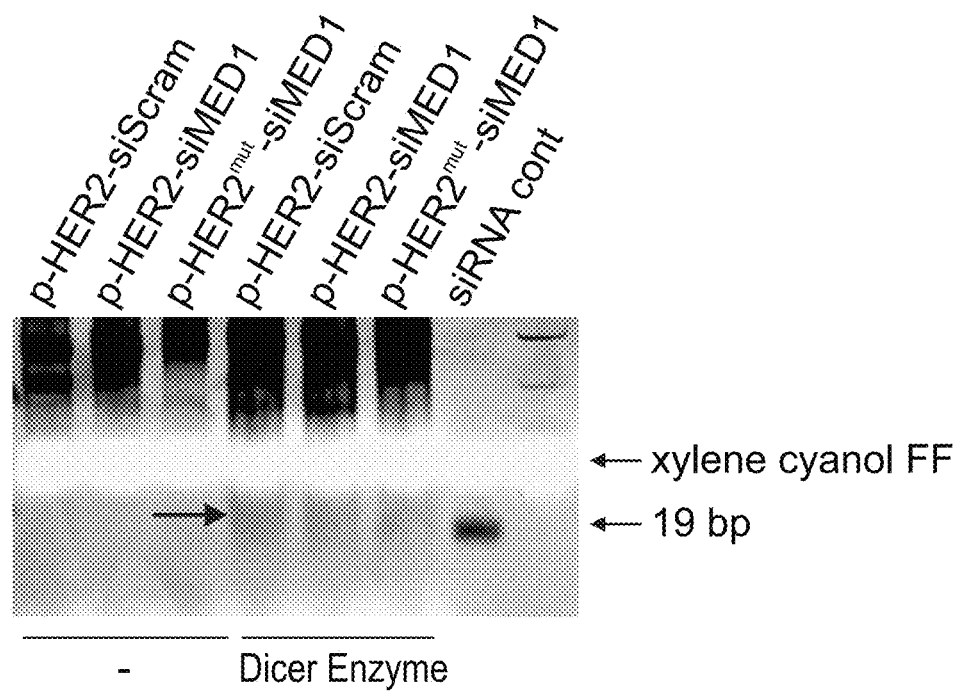
Fig. 7D
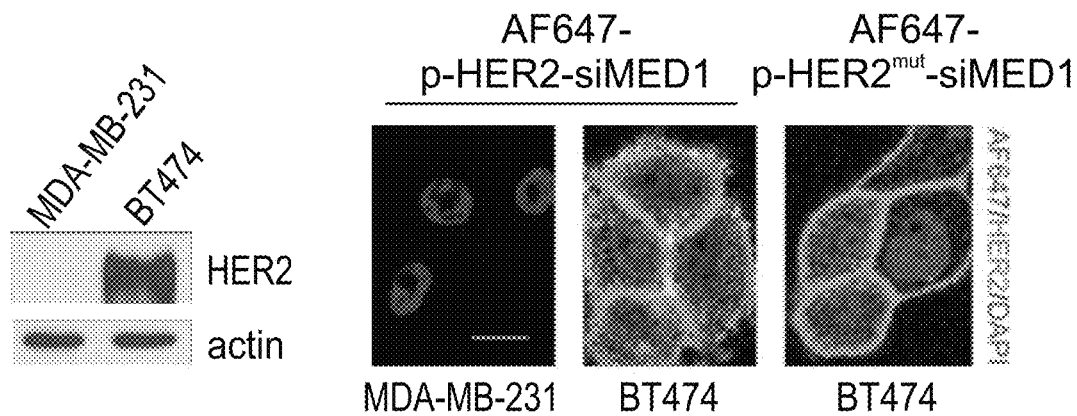
Fig. 8A
Fig. 8B

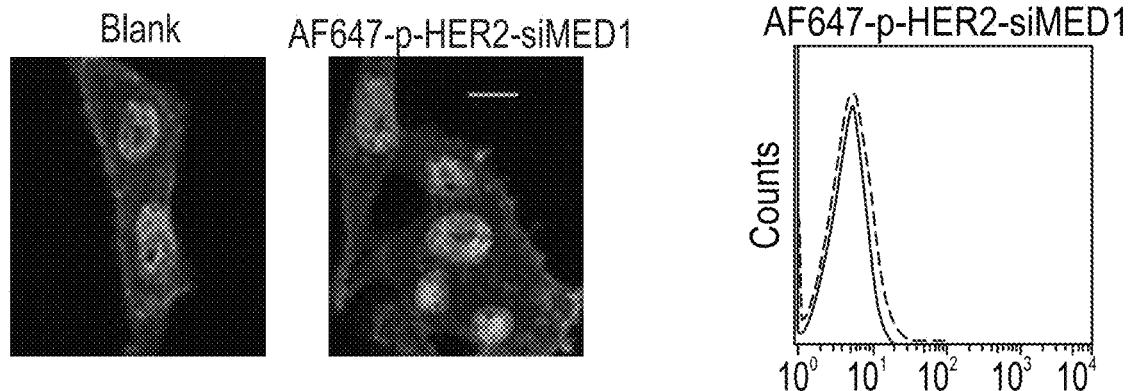
Fig. 8C
Fig. 8D
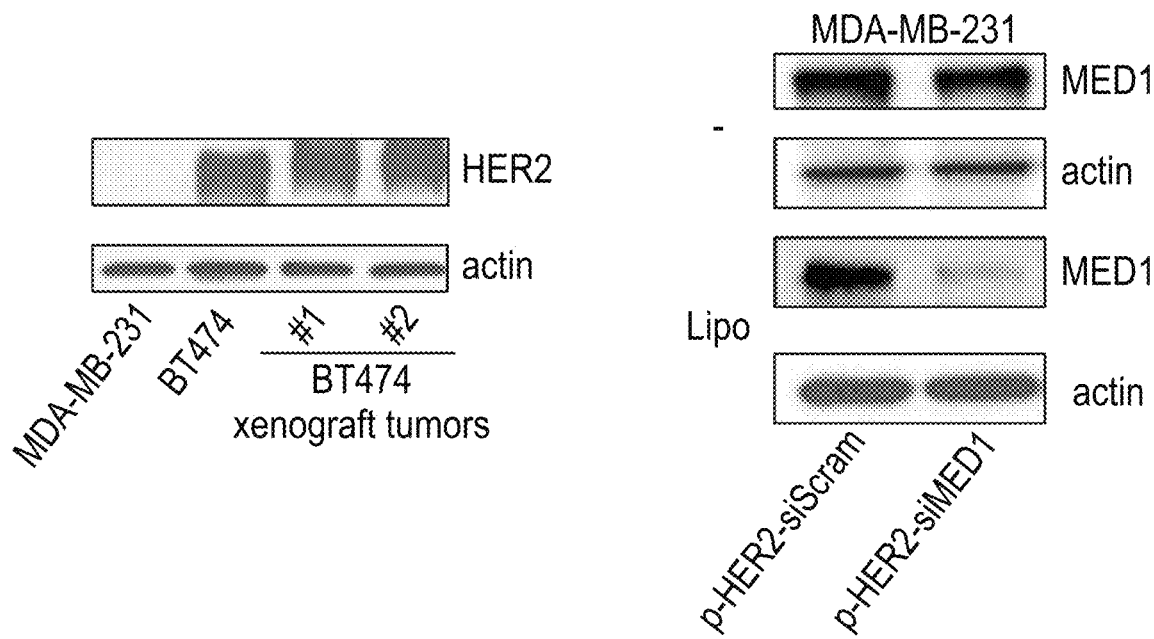
Fig. 8E
Fig. 8F

MULTIFUNCTIONAL RNA NANOPARTICLES AND METHODS FOR TREATING CANCER AND THERAPEUTIC RESISTANT CANCER

PRIORITY CLAIM

This application claims priority to U.S. Provisional No. 62/431,640 filed Dec. 8, 2016, the entire disclosure of which is incorporated herein by this reference.

GOVERNMENT LICENSE RIGHTS

This invention was made with government support under contract no. R01CA197865 awarded by the National Institute of Health. The government has certain rights in the invention.

BACKGROUND

Breast cancer has continually been one of the leading malignant cancers threatening global human health. Approximately 75% of patients express estrogen receptor alpha (ERα), which belongs to the steroid nuclear receptor family and has been well documented in promoting breast carcinogenesis in an estrogen-dependent manner. Hence, tamoxifen, an antagonist of ERα, has been widely used as a first-line adjuvant endocrine therapy to treat both premenopausal and postmenopausal ERα-positive breast cancer patients. Unfortunately, about half of these patients have intrinsic or acquired tamoxifen resistance, which significantly limits the clinical outcome of tamoxifen treatment (Osborne, C. K. et al. "Mechanisms of Endocrine Resistance in Breast Cancer" Annu. Rev. Med. 2011, 62, 233-247, incorporated by reference). Recent research has provided deeper insight into the molecular mechanisms involved in tamoxifen resistance (Ali, S. et al. "Endocrine-Responsive Breast Cancer and Strategies for Combating Resistance" Nat. Rev. Cancer 2002, 2, 101-112, incorporated by reference). Most notably, overexpression of HER2 has been shown to be one of the major mechanisms associated with tamoxifen resistance by enhancing ERα functions. Moreover, recent studies have further revealed the key role of the crosstalk between HER2 and ERα transcriptional coactivator Mediator Subunit 1 (MED1) in tamoxifen resistance (Luoh, S. W. Cancer Genet. Cytogen. 2002, 136, 43-47, and Cui, J. et al. Cancer Res. 2012, 72, 5625-5634, both incorporated by reference).

As a transcriptional co-activator of ERα, MED1 is associated with a subpopulation of the TRAP/mediator complex, and directly interacts with ERα via its two classical LxxLL motifs to facilitate target gene expression through the recruitment of RNA polymerase II and general transcriptional machinery. Interestingly, the MED 1 gene is located in close proximity to the HER2 gene within the HER2 amplicon on chromosome 17q12 and co-amplifies with HER2 in almost all cases. Our recent studies have further confirmed that MED1 protein level highly correlated with HER2 status in human breast cancer by tissue microarray analyses.[11] Importantly, MED1 can be phosphorylated and activated by HER2 signaling pathway, while knockdown of MED1 by small interference RNA (siRNA) significantly sensitized HER2-overexpressing ERα positive breast cancer cells to tamoxifen treatment (Cui, J. et al. Cancer Res. 2012, 72, 5625-5634). Significantly, clinical data further indicated that MED1 overexpression strongly correlates with endocrine therapy resistance in ERα-positive breast cancer patients (Ross-Innes, C. S. et al. Nature 2012, 481, 389-393, and Nagalingam, A. et al. Carcinogenesis 2012, 33, 918-930, both incorporated by reference).

Since the discovery and establishment of gene silencing by RNA interference at the turn of the century, many siRNA-based drugs have entered clinical trials with a number of them recently showing promising outcomes. However, developing siRNA delivery systems with strong stability, specific tumor targeting ability, and low toxicity remains a major challenge. Recently, three-way junction (3-WJ) pRNA nanoparticles, which are derived from the RNA of bacteriophage phi29 DNA packaging motor, have shown promise as a highly desirable in vivo siRNA delivery system (Guo, P., Nat. Nanotechnol. 2010, 5, 833-842, and Shu, Y. et al. Adv. Drug Deliv. Rev. 2014, 66, 74-89, both incorporated by reference). Using RNA nanotechnology, Phi29 pRNA has been utilized to "bottom-up" assemble a variety of dimers, trimers, hexamers, tetramers and higher-order oligomers with controllable stoichiometry. The extending arms of pRNA structures could be intelligently replaced with siRNAs, miRNAs, riboswitches, RNA aptamers, and conjugated with fluorescent probes or other moieties to construct multifunctional pRNA nanoparticles. Notably, the 2'-fluoro modification of RNA bases rendered the pRNA nanoparticles ultra-stable and resistant to RNase exposure (Liu, J. et al. ACS Nano 2011, 5, 237-246, incorporated by reference). Moreover, after systemic administration, the pRNA nanoparticles demonstrated a favorable pharmacokinetic profile with a highly prolonged half-life and excellent biosafety in mice (Abdelmawla, S. et al. Mol. Ther. 2011, 19, 1312-1322, incorporated by reference). These pRNA nanoparticles have been applied previously to specifically target a variety of human tumors and tested for cancer therapy.

SUMMARY

Accordingly, embodiments of the invention provide a three-way junction (3-WJ) pRNA-HER2apt-siMED1 nanoparticle specifically designed and self-assembled to target HER2-overexpressing human cancer by utilizing a HER2 RNA aptamer, and to deliver MED1 siRNA to the cancer cells to effectively silence MED1 expression, as well as methods comprising administering pharmaceutical compositions comprising the inventive nanoparticles to patient suffering from HER2-implicated cancer, for example, breast, uterine, ovarian, stomach, bladder, lung or salivary cancer, and in particular to patients suffering from breast cancer and exhibiting primary or acquired resistance to treatment with anti-estrogenic agents such as tamoxifen. The inventive nanoparticles specifically bind to HER2-overexpressing breast cancer cells, efficiently deplete MED1 expression and significantly decrease ERα-mediated gene transcription.

One embodiments is directed to three-way junction (3-WJj) pRNA nanoparticles comprising a HER2-targeting RNA aptamer and two different Mediator Subunit 1(MED1) silencing RNAs (siRNAs) designed for targeted delivery of MED1-siRNA to HER2 receptors, as well as pharmaceutical compositions formulated for local or systemic administration comprising at least one pRNA-HER2apt-MED1-siRNA nanoparticle, and in some embodiments, at least one anti-estrogenic agent.

One embodiment is directed to methods for selectively inhibiting expression of MED1 in HER2-overexpressing cells comprising administering a pharmaceutical composition comprising at least one pRNA-HER2apt-MED1-siRNA. Embodiments are also directed to methods for threating humans suffering from HER2-implicated cancer, and in particular HER2-positive breast cancer, the methods comprising administering a pharmaceutical composition comprising at least one pRNA-HER2apt-MED1-siRNA nanoparticle.

Some embodiments are directed to methods for sensitizing breast cancer cells to treatment with an anti-estrogenic agent, the method comprising treating the breast cancer cells with 2'F-modified pRNA-HER2apt-MED1-siRNA nanoparticles.

Other embodiments are directed to methods for treating a patient suffering from primary or acquired tamoxifen-resistant breast cancer, the method comprising administering a pharmaceutical composition comprising 2'F-modified pRNA-HER2apt-MED1-siRNA nanoparticles.

Another embodiment is directed to methods for inhibiting migration and metastasis of cancer cells, and cancer stem cell formation, in a patient suffering from breast cancer, the method comprising treating the patient by administering a composition comprising pRNA-HER2apt-siMED1 nanoparticles.

Summarily, embodiments of the invention provide multifunctionalized RNA nanoparticles that specifically target HER2-overexpressing human breast cancer, silence MED1 and overcome tamoxifen resistance.

These and other embodiments are detailed and further clarified by reference to the Figures and Detailed Description set forth below.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A) The scheme of the pRNA-HER2apt-siMED1 (p-HER2-siMED1) (SEQ ID NO: 15) structure. FIG. 1B) The p1 and p2 strands of pRNA-HER2apt-siMED1_were transcribed using an in vitro RNA transcription system and separated in 8% denatured PAGE gel. FIG. 1C) pRNA-HER2apt-siMED1 nanoparticles were generated by annealing equal molar of strands p1 and p2, and subjected to 8% native PAGE gel electrophoresis. FIG. 1D) DLS assay of hydrodynamic size of pRNA-HER2apt-siMED1 nanoparticle. FIG. 1E) The Tm value of pRNA-HER2apt-siMED1 nanoparticle determined by TGGE assay. FIG. 1F) The atomic force microscopy (AFM) images of pRNA-HER2apt-siMED1 nanoparticles. FIG. 1G) The stability of control unmodified and 2'-F modified pRNA nanoparticles was examined by 8% native PAGE gel electrophoresis after RNase A, 10% FBS-supplemented DMEM medium and 8M urea treatments for the indicated time at 37° C.

FIG. 2A) Confocal microscopy analyses of the internalization of AF647-labeled control and pRNA-HER2apt-siMED1 nanoparticles by BT474 cells. Scale bar: 10 μm. FIG. 2B) Flow cytometry assays of the cellular uptake of AF647-labeled control and pRNA-HER2apt-siMED1 nanoparticles by BT474 cells. FIG. 2C) IVIS Lumina live imaging of BT474 orthotopic xenograft mice 24 hrs after i.v. injection of indicated AF647-labeled pRNA nanoparticles (10 mg/Kg). FIG. 2D) Major organs and tumors of above mice were excised and imaged for AF647 fluorescence. FIG. 2E) Frozen tumor sections were examined for localization of AF647-labeled pRNA nanoparticles (red) using confocal microscopy. The blood vessels were stained with anti-CD31 primary antibody and Alexa488-conjugated secondary antibody (green). The nuclei were stained with DAPI (blue). Scale bar: 50 μm. FIG. 2F) The fluorescence intensity of AF647-labeled pRNA nanoparticles (red) in frozen tumor sections was quantified with Image-pro Plus software.

FIG. 3A) BT474 cells were incubated with 10 μg/mL control and pRNA-HER2apt-siMED1 nanoparticles for 48 h, and MED1 mRNA level was determined by real-time PCR. FIG. 3B) BT474 cells were incubated directly with (as indicated by -) or transfected with indicated pRNAs using lipofectamine 2000. At 48 h post treatment, MED1 protein levels were determined by western blotting. FIG. 3C) BT474 cells were treated with 10 μg/mL pRNA nanoparticles for 48 h and assayed for cell viability by MTT assay. FIG. 3D) Cells were treated as above and seeded for migration, and FIG. 3E) invasion transwell assays. Scale bar: 50 μm. FIG. 3F) After pRNA treatment for 48 h, the mRNA levels of ERα target genes TFF-1, FIG. 3G) c-Myc, and FIG. 3H) cyclin D1 in BT474 cells were determined by real-time PCR.

FIG. 4A) BT474 cells were treated with pRNA nanoparticles in combination with vehicle or 1 μM 4-hydroxytamoxifen (4-OHT) as indicated for 48 h, and assayed for cell viability by MTT assay. FIG. 4B) Cells were treated as above and the migration and FIG. 4C) invasion capabilities were examined. FIG. 4D) Cells were treated as above and assayed for in vitro mammosphere formation. FIG. 4E) The number of mammospheres was counted, and FIG. 4F) the mammosphere size was calculated. Scale bar: 10 μm.

FIG. 5A) BT474 orthotopic xenograft mouse models were treated with control pRNA-HER2apt-siScram or pRNA-HER2apt-siMED1 (4 mg/Kg) once a week, in combination with vehicle or tamoxifen (TAM, 0.5 mg/mice/day) 5 days per week. Tumor sizes were measured every three days. FIG. 5B) After three weeks, mice were i.p. injected with D-luciferin, and representative in vivo images of BT474 tumors were recorded using IVIS Lumina imaging system. FIG. 5C) Average weight of the tumors excised at the end of the treatment, and FIG. 5D) the representative photos of tumors. FIG. 5E and FIG. 5F) MED1 expression in the BT474 tumors was examined using IHC staining and FIG. 5G) immunoblotting. FIG. 5H) The expression of Ki-67 in tumor tissues was analyzed using IHC staining, and FIG. 5I) the percentage of Ki-67 positive cells was counted. Scale bar: 100 μm.

FIG. 6A) Whole lung tissues were fixed, embedded, and sectioned for H&E staining, and FIG. 6B) metastasis foci in the whole lung tissues were then counted. Arrow indicates the metastasis foci. Scale bar: 100 μm. FIG. 6C) After digesting tumor tissues with trypsin and 0.1% collagenase, tumor cells were stained for CD44 and CD24, and FIG. 6D) analyzed for $CD44^+CD24^{-/low}$ stem cell population using flow cytometry. FIG. 6E) Total RNA in the tumor tissues was extracted using TRIZOL reagent, and the expression of TFF-1, FIG. 6F) c-Myc, FIG. 6G) cyclin D1, and FIG. 6H) MMP-9 were determined by real-time PCR.

FIGS. 7A-7D. HER2-targeting RNA aptamers and testing for MED1 siRNA delivery and siRNA release from pRNA nanoparticles.

FIG. 7A) Six HER2-targeting RNA aptamers were selected from previous literatures, and their secondary structures were predicted using Srna-fold software. FIG. 7B) Six p2 strands containing the six different HER2 RNA aptamers were synthesized and annealed with the same p1 strand to generate six different pRNA-HER2apt-MED1 siRNA nanoparticles, respectively, followed by examination using 8% native PAGE gel electrophoresis. FIG. 7C) BT474 cells were treated with above pRNA nanoparticles for 48 h, and then MED1 protein level was determined by western blotting. Red arrow indicates the pRNA nanoparticles with B3 aptamer had the best efficiency in MED1 silencing. FIG. 7D) 1 μg pRNA nanoparticles were incubated with recombinant Dicer enzyme (Genlantis) at 37° C. for 12 h, the product was separated by 8% native PAGE gel.

FIGS. 8A-8F. Demonstrate that pRNA-HER2apt-siMED1 nanoparticles targeted HER2-overexpressing BT474 cells but not HER2-negative MDA-MB-231 cells.

FIG. 8A) HER2 expression in BT474 and MDA-MB-231 cells determined by western blot analyses. FIG. 8B) The binding of AF-647-labeled pRNA-HER2apt-siMED1 and its mutant nanoparticles to MDA-MB-231 and BT474 cells examined by confocal microscopy. Green represents the immunofluorescent staining of HER2, and blue represents nuclear staining with DAPI. FIG. 8C) The internalization of AF647-labeled pRNA nanoparticles by MDA-MB-231 cells examined by confocal microscopy. Green represents the immunofluorescent staining of β-actin. Scale bar: 10 μm. FIG. 8D) The cellular uptake of AF647-labeled pRNA nanoparticles by MDA-MB-231 cells quantified by flow cytometry. FIG. 8E) HER2 expression in BT474 xenograft tumors was examined by western blot analyses. FIG. 8F) MDA-MB-231 cells were incubated directly with (as indicated by-) or transfected with pRNAs using lipofectamine 2000. At 48 h post treatment, MED1 protein levels were determined by western blots.

FIG. 9A) BT474 cells were treated with different concentrations of pRNA nanoparticles as indicated for 48 h. After that, MED1 protein level was determined by western blots, and FIG. 9B) the cell viability was determined by MTT assay.

FIG. 10A) Two HER2-overexpressing breast cancer cell lines MCF7/TAM and FIG. 10B) MCF7/HER2, were treated with 10 μg/mL pRNA-HER2apt-siMED1 nanoparticles or scramble control for 48 h, and then MED1 protein level was determined using western blots. FIG. 10C) MCF7/TAM and FIG. 10D) MCF7/HER2 cells were treated with 10 μg/mL pRNA nanoparticles and/or 1 μM tamoxifen (TAM) as indicated for 48 h, and then cell growth was determined using an MTT assay.

FIG. 12A) During therapeutic treatment to orthotopic xenograft mouse models, the body weights of mice were recorded every three days. FIG. 12B) After therapeutic treatment, major organs were excised, fixed in 10% neutral formalin buffer, embedded in paraffin, sectioned and examined for histopathology by H&E staining. Scale bar: 100 μm.

DETAILED DESCRIPTION

Figure 1A:
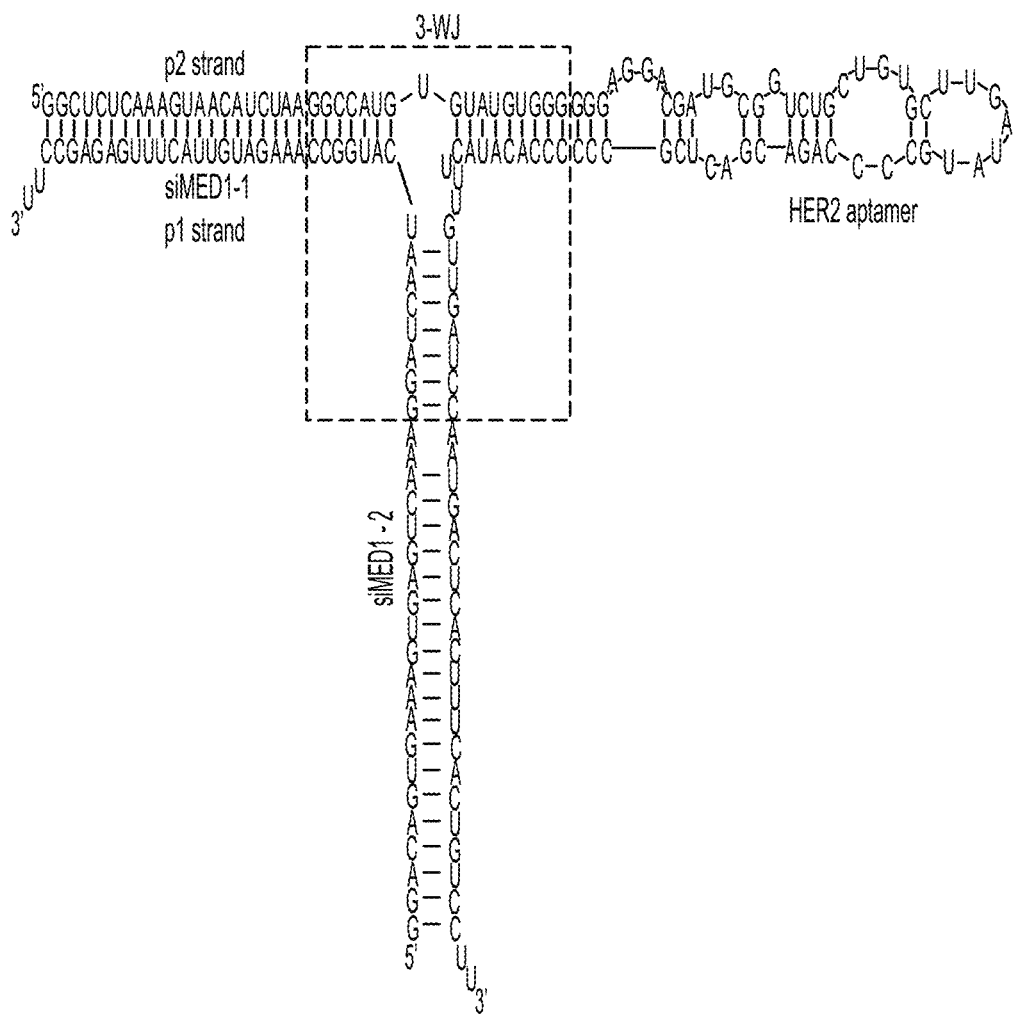
FIGS. 1A-1G. Set forth construction and characterization of pRNA-HER2apt-siMED1 nanoparticles.

The packaging RNA (pRNA) of the bacteriophage phi29 DNA packaging motor was previously developed into an effective nanoparticle delivery platform (Nature Protocols 8, 1635-1659, 2013, the entire disclosure of which is incorporated herein). Three "toolkits" are derived from the pRNA structural features: interlocking loops, palindrome sequences, and an RNA three-way junction (3-WJ) for branch extension. Biologically relevant molecules or molecules with a desired function, including siRNA, ribozymes, aptamers, chemical ligands, fluorophores, e.g., may be fused to the pRNA prior to self-assembly of the nanoparticle to ensure production of homogenous molecules and retention of native/appropriate folding and functionality of the incorporated molecules. pRNA nanoparticles have been shown to be thermodynamically and chemically stable and may be formulated for systemic delivery, where they are shown to accumulate in target tissue and to avoid accumulation in other organs.

Most breast cancers express estrogen receptor (ER) α, and the anti-estrogen drugs such as tamoxifen has been widely used for their treatment. Unfortunately, up to half of all ERα-positive tumors have intrinsic or acquired endocrine therapy resistance. Recent studies by the present investigators revealed that the ER coactivator Mediator Subunit 1 (MED1) plays a critical role in tamoxifen resistance through cross-talk with HER2.

Phi29-derived 3-WJ pRNA nanoparticles provide a highly desirable delivery system for the inventive assemblies described herein. In addition to the uniform nano-scale size, precise stoichiometry and excellent stability and biocompatibility, the extended arms of the 3-WJ motif are easily replaced with siRNAs and specific RNA aptamers without impairment of the ultrastability and conformation. The designed and assembled pRNA-HER2apt-siMED1 nanoparticles are ultra-compact (8.68±1.87 nm) and have a very high Tm value (78±2° C.), which greatly favor not only their serum stability but also their accumulation to tumors after systemic administration due to a combination of enhanced permeability and retention (EPR) effect and selective targeting capability of the HER2 aptamer (Cabral, H. et al. Nat. Nanotechnol. 2011, 6, 815-823, incorporated by reference). Significantly, it was discovered that the pRNA nanoparticles could be utilized to combat endocrine therapy resistance, a major obstacle in current breast cancer treatment. Aside from its notable anti-breast cancer activity, pRNA-HER2apt-siMED1 nanoparticle was also discovered to greatly sensitize HER2-overexpressing breast cancer to tamoxifen treatment while eliciting no apparent toxicity to the normal organs after systemic administration, thus providing a very promising siRNA delivery platform for cancer therapy.

HER2 is a well-known driver and biomarker for tamoxifen-resistant human breast cancer. HER2 monoclonal antibodies including trastuzumab and pertuzumab have been widely used to treat breast cancer patients (Rimawi, M. F. et al. *Annu. Rev.Med.* 2015, 66, 111-128, and Amiri-Kordestani, L. et al. *Cancer Res.* 2014, 20, 5359-5364, incorporated by reference). They have also been used for conjugation with chemotherapeutic drugs, such as emtansine, or nanocarriers for targeted drug delivery (Hurvitz, S. et al. *J. Clin. Oncol.* 2013, 31, 1157-1163 and Calce, E. et al. *Curr. Med. Chem.* 2015, 22, 2525-2538, incorporated by reference). Recently, RNA aptamers have emerged as promising targeting moieties for cancer diagnosis and therapy, and a number of HER2 RNA aptamers have been isolated through SELEX methods and tested in vitro (Thiel, K. et al. *Nucleic Acids Res.* 2012, 40, 6319-6337, and Kim, M. Y. et al. *Nucleic Acid Ther.* 2011, 21, 173-178, incorporated by reference). Nucleotide modification, such as 2'-fluoro, 2'-O-methyl and 2'-amine modification, has now significantly improved the RNA stability under physiological conditions. In addition, RNA aptamers have several advantages for targeting, including small size, lower cost, convenient optimization and conjugation. However, the potential of these HER2 RNA aptamers for in vivo targeting and drug delivery was not previously examined.

Embodiments of the invention provide specific aptamers tested and identified as capable of targeting HER2-overexpressing breast cancer cells and delivering MED1 siRNAs both in vitro and in vivo. Significantly particular HER2 aptamers not only specifically targeted the orthotopic xenograft tumors, but also delivered siRNAs to dramatically silence MED1 expression in tumor tissues. The observed greatly enhanced penetration and accumulation of pRNA-HER2apt-siMED1 nanoparticles into tumor cells is likely attributable to the specific targeting since the pRNA nanoparticles with mutant HER2 aptamers largely remained in the tumor blood vessels. Hence, embodiments are directed to application of HER2 RNA aptamers in the development of a targeted drug delivery systems for HER2-overexpressing human breast cancer.

According to embodiments disclosed and claimed herein, the 3-WJ pRNA structure is exploited to construct AlexaFluor647-labeled multifunctional pRNA-HER2apt-siMED1 nanoparticles bearing a HER2-targeting RNA aptamer and two different MED1 siRNAs to silence MED1 expression in HER2-overexpressing ERα-positive breast cancer cells. The pRNA-HER2apt-siMED1 nanoparticles exhibit high Tm value and excellent stability upon exposure to 8 M urea, RNase A, and serum. Significantly, these nanoparticles are shown to specifically target HER2-overexpressing breast cancer to silence MED1 expression both in vitro and in orthotopic xenograft mouse models. Specific embodiments of the invention provide pRNA-HER2apt-siMED1 nanoparticles that specifically deliver MED1 siRNAs to HER2-overexpressing human breast cancer and overcome tamoxifen resistance. Embodiments of the invention provides a pRNA nanoparticle functionalized for targeted delivery of Mediator Subunit 1(MED1) silencing RNA (siRNA) to human breast cancer cells via human epidermal growth factor receptor 2 (HER2) receptors, the pRNA nanoparticle comprising: pRNA, a HER2-targeting RNA aptamer, and at least one MED1 siRNA. In specific embodiments, the pRNA comprises of one or more oligionucleotide strands annealed to form the RNA nanoparticle.

The human MED1 siRNAs used were selected based on their ability to knockdown MED1 in in vitro functional assays. Additional human MED1 siRNA suitable for incorporation into the pRNA to form embodiments of the inventive nanoparticles are also available from a number of well-known suppliers, including ThermoFisher Scientific (www.thermofisher.com/order/genome-database/browse/sirna/gene/MED1), and Applied Biological Materials, Inc. (www.abmgood.com/MED1-siRNA-Lentivector-MED1). According to specific embodiments, the pRNA nanoparticle comprises two siRNAs, and according to even more specific embodiments, the pRNA nanoparticle comprises two different MED1 siRNAs.

RNA apatmers are defined generally as RNA oligonucleotides that bind to a specific target with high affinity and specificity. Aptamers are chemically synthesized, then selected for a desired binding profile through the well-known SELEX process and derivations such as Cell-SELEX and Tissue-SELEX. Generally, an RNA aptamer is between 56 and 120 nucleotides long and is comprised of a variable region and a constant region. The variable region is a center-located region of between about 20 and 80 nucleotides. Constant regions are found on both the 5' and 3' sides of the variable region and are each about 18-20 nucleotides. The HER2 family of receptor tyrosine kinasesare known to play a major role in the formation and progression of human tumors.

Amplification and/or overexpression of HER2 have been reported in numerous cancers including breast, uterine, ovarian, stomach, bladder, salivary, and lung cancers etc. HER2 has been a target for the treatment of advanced cancers and RNA aptamers specific for the extracellular domain of HER2 are known (generally selected from an RNA library of 2'-fluorine-modified RNA transcripts). After a sufficient number of selection cycles, high-affinity RNA aptamers may be isolated. Binding patterns are then evaluated to ultimately identify aptamers specific to the extracellular domain of the HER2 protein. According to very specific embodiments, the pRNA nanoparticle is fabricated to comprise HER2-targeting RNA aptamer selected from MINI (SEQ ID NO: 7), A1 (SEQ ID NO: 8), B3 (SEQ ID NO: 9), C3 (SEQ ID NO: 10), D3 (SEQ ID NO: 11) and E1 (SEQ ID NO: 12). The RNA aptamer component targets the nanoparticle to the HER2 receptor where the MED1 siRNA is delivered through the receptor to the cancer cell, for example the breast cancer cell. Although experiments disclosed herein are specific to breast cancer, it will be clear to a person of ordinary skill in the art that upon systemic administration, the inventive nanoparticles and therapies based thereon will effectuate deliver of a desired siRNA to HER2 receptors throughout the body and although exemplified with breast cancer, the inventive particles may be readily adapted for treatment of other HER2-over expressing cancers. According to very specific examples, a pRNA nanoparticle effective for the treatment of breast cancer is selected from one or more of pRNA-HER2mini apt-MED1-siRNA, pRNA-HER2A1 apt-MED1-siRNA, pRNA-HER2B3 apt-MED1-siRNA, pRNA-HER2C3 apt-MED1-siRNA, pRNA-HER2D3 apt-MED1-siRNA, and pRNA HER2E1 apt-MED1-siRNA. In some embodiments the RNA aptamer comprises a 2'F-modification. According to very specific embodiments, a pRNA nanoparticle comprises 2'F-modified 3-WJ pRNA-HER2B3 apt-MED 1-siRNA.

Generally, embodiments of the pRNA nanoparticles fabricated as described herein comprise an average diameter of about 5 to about 15 nm as measured by DLS scattering, and in more specific embodiments comprise an average diameter of from about 7 to about 11 nm as measured by DLS scattering.

Another embodiment of the invention is directed to pharmaceutical compositions formulated for local or systemic administration to a patient suffering from a HER2-overexpressing cancer. The compositions comprise one or more pRNA nanoparticles according to embodiments of the invention, and a pharmaceutically acceptable vehicle, and, optionally, one or more pharmaceutical excipients. Suitable vehicles and excipients as a function of desired route of administration are disclosed, for example, in "Delivery Technologies for Biopharmaceuticals: Peptides, Proteins, Nucleic Acids and Vaccines," ed. Jorgensen & Nielson, John Wiley & Sons, 2009, and "Nanomedicine in Drug Delivery, ed. Kumar, Mansour, Friedman & Blough, CRC Press, 2013, the entire disclosures of which are incorporated herein by this reference. According to specific embodiments, the compositions further comprise at least one anti-estrogenic agent. Non-limiting examples include Tamoxifen, Toremifene, Fulvestrant, Raloxifene, lasofoxifene, Bazedoxifene, RAD-1901 and an aromatase inhibitor (AI) (non-limiting examples of suitable AIs include Letrozole, Anastrozole, Exemestane, and combinations thereof). As disclosed herein, the inventive nanoparticles are particularly effective in the treatment of cancers that have innate or acquired resistance to anti-estrogenic agents such as Tamoxifen.

Another embodiment is directed to methods for selectively inhibiting expression of MED1 in HER2-overexpressing cells by administering a pharmaceutical composition. HER2-overexpressing cells are often found in human tumors and it is contemplated that the inventive nanoparticles and pharmaceutical compositions are predictably effective for delivery of MED1 siRNA to HER2 and most desirably to HER2-overexpressing cells characteristic of all HER2-implicated cancers. Embodiments provide methods for treating a human suffering from breast, uterine, ovarian, stomach, bladder, salivary and lung cancer. According to very specific embodiments, methods comprise administering a pharmaceutical composition comprising at least one pRNA nanoparticle comprising pRNA, a HER2-targeting RNA aptamer, and at least one MED1 siRNA to a patient suffering from breast cancer. According to specific embodiments, the HER2-targeting RNA aptamer is selected from MINI, A1, B3, C3, D3, and E1, and according to very specific embodiments, the RNA aptamer is 2'F-modified and the pRNA nanoparticle is selected from pRNA-HER2mini apt-MED1-siRNA, pRNA-HER2A1 apt-MED1-siRNA, pRNA-HER2B3 apt-MED1-siRNA, pRNA-HER2C3 apt-MED1-siRNA, pRNA-HER2D3 apt-MED1-siRNA, and pRNA-HER2E1 apt-MED1-siRNA. According to even more specific method embodiments, the pRNA nanoparticle comprises 2'F-modified 3-WJ pRNA-HER2B3 apt-MED1-siRNA.

As empirically demonstrated herein, specifically designed pRNA nanoparticle embodiments are particularly effective for treating cancer that exhibits primary or acquired resistance to anti-estrogenic agents. In some embodiments, HER2-over expressing cancer cells, such as breast cancer cells, may be sensitized to treatment with an anti-estrogenic agent by administering embodiments of the inventive nanoparticles, for example in a very specific embodiment, by administering 2'F-modified pRNA-HER2apt-MED1-siRNA nanoparticles, and in even more specific embodiments, by administering pRNA nanoparticles selected from pRNA-HER2mini apt-MED1-siRNA, pRNA-HER2A1 apt-MED1-siRNA, pRNA-HER2B3 apt-MED1-siRNA, pRNA-HER2C3 apt-MED1-siRNA, pRNA-HER2D3 apt-MED1-siRNA, and pRNA-HER2E1 apt-MED1-siRNA, and combinations thereof. "Treating" as utilized in some embodiments comprises administering the pRNA nanoparticles before, cotemporaneous with, or subsequent to treatment with an anti-estrogenic agent.

According to one embodiment, methods are provided for treating a patient suffering from primary or acquired tamoxifen-resistant cancer, for example breast cancer, comprising administering a pharmaceutical composition comprising 2'F-modified pRNA-HER2apt-MED1-siRNA nanoparticles selected from pRNA-HER2mini apt-MED1-siRNA, pRNA-HER2A1 apt-MED1-siRNA, pRNA-HER2B3 apt-MED1-siRNA, pRNA-HER2C3 apt-MED1-siRNA, pRNA-HER2D3 apt-MED1-siRNA, and pRNA-HER2E1 apt-MED1-siRNA. Pharmaceutical compositions may be formulated for systemic or local delivery, and in specific embodiments are formulated for systemic delivery having the pRNA nanoparticle is present in a concentration of from about 2 µg/mL to about 10 µg/mL by volume of the composition.

Cancer metastasis and cancer stem cells are the key drivers for therapy resistance and tumor recurrence. Significantly, experimental evidence set forth herein indicates that the pRNA-HER2apt-siMED1 nanoparticles reduce both breast cancer metastasis and cancer stem cells (CSCs). CSCs are similar to adult stem cells and possess the ability for unlimited self-renewal and are implicated in cancer development, metastasis and drug resistance. Standard cancer treatments only eliminate rapidly proliferating cancer cells (non-CSCs), whereas CSCs are relatively quiescent and not only avoid cell death, but may even be enriched in a recurring tumor. CSCs are therefore widely considered to be the root of relapse and metastasis.

The pRNA-HER2apt-siMED1 nanoparticles not only eliminated tumor lung metastasis in orthotopic xenograft murine models, but also dramatically reduced $CD44^+$ $CD24^{-/low}$ cancer stem cells in combination with tamoxifen. Consistent with these findings, it was discovered that their migration and invasion capabilities and the expression of a number of key ERα-associated genes involved in metastasis and cancer stem cell formation are greatly inhibited by pRNA-HER2apt-siMED1 nanoparticles. These data suggest that the pRNA-HER2apt-siMED1 nanoparticles could be more advantageous by targeting both of these processes than most other currently available regimens only capable of targeting one such process. Finally, although only its combinational use with tamoxifen has been tested, combinational use with other anti-estrogens (non-limiting examples include fulvestrant, toremifene, and aromatase inhibitors such as letrozole, anastrozole, or exemestane,) is contemplated along with additional anti-HER2 therapies.

Thus, methods for inhibiting migration and metastasis of cancer cells, and for inhibiting cancer stem cell formation are also provided, the methods comprising administering a composition comprising pRNA-HER2apt-siMED1 nanoparticles to a patient suffering from a HER2-implicated cancer such as breast, uterine, stomach, ovarian, salivary, bladder or lung cancer. Specific embodiments further comprise administering at least one anti-estrogenic agent. The anti-estrogenic agent may be administered before, cotemporaneous with, or subsequent to, administering the composition comprising embodiments of the pRNA nanoparticles. Non-limiting examples of anti-estrogenic agents include Tamoxifen, Toremifene, Fulvestrant, one or more aromatase inhibitors selected from letrozole, anastrozole and exemestane, and combinations thereof. According to very specific examples, the anti-estrogenic agent comprises Tamoxifen.

The crosstalk between MED1 and HER2 plays an important role in the tamoxifen resistance of human breast cancer. Targeted MED1 silencing in HER2-overexpressing ERα-positive human breast cancer is a promising strategy to overcome tamoxifen resistance. Embodiments of the invention provide pRNA-HER2apt-siMED1 nanoparticles for HER2-targeted MED1 siRNA delivery. Empirical work set forth herein demonstrates that the pRNA-HER2apt-siMED1 nanoparticles are specifically delivered to HER2-overexpressing ERα-positive breast cancer cells both in vitro and in vivo. These RNA nanoparticles successfully silenced MED1 expression and attenuated ERα function, consequently suppressing cancer cell proliferation and tumor growth. In combination with tamoxifen treatment, these nanoparticles notably decreased tumor lung metastasis and cancer stem cells content, thereby further reducing tumor burden in orthotopic xenograft mouse models. Methods are provided for treating a patient suffering from primary or acquired tamoxifen-resistant cancer, for example breast cancer, comprising administering a pharmaceutical composition comprising 2'F-modified pRNA-HER2apt-MED1-siRNA nanoparticles selected from pRNA-HER2mini apt-MED1-siRNA, pRNA-HER2A1 apt-MED1-siRNA, pRNA-HER2B3 apt-MED1-siRNA, pRNA-HER2C3 apt-MED1-siRNA, pRNA-HER2D3 apt-MED1-siRNA, and pRNA-HER2E1 apt-MED1-siRNA. Pharmaceutical compositions may be formulated for systemic or local delivery, and in specific embodiments are formulated for systemic delivery having the pRNA nanoparticle is present in a concentration of from about 2 µg/mL to about 10 µg/mL by volume of the composition.

The Examples set forth herein demonstrate that the pRNA nanoparticles not only reduce the growth, metastasis and mammosphere formation of the HER2-overexpressing breast cancer cells, but also sensitize them to tamoxifen treatment. The nanoparticles are demonstrated to be bio-safe and to efficiently target and penetrate into HER2-overexpressing tumors after systemic administration in orthotopic xenograft mouse models. In addition to their ability to greatly inhibit tumor growth and metastasis, the novel nanoparticles also lead to a dramatic reduction in the stem cell content of breast tumors when combined with tamoxifen treatment in vivo.

The following examples are set forth to illustrate various aspects and specific embodiments and should not be construed as limiting the full scope of the invention as defined by the appended claims.

EXAMPLES

The following detailed methodologies are applicable as noted to Examples 1-5 set forth below.

Methods/Experimental

Cell culture. Human breast cancer luciferase-overexpressing BT474 and MDA-MB-231 cells were maintained in DMEM medium (Hyclone, Thermo Scientific) supplemented with 10% fetal bovine serum (FBS, Sigma) and 1% penicillin/streptomycin (Corning) at 37° C. in a humidified atmosphere with 5% CO2.[53]

Generation of pRNA nanoparticles. The two strands of pRNA were synthesized with the DNA templates, which were amplified with overlapping primers (Sigma) by PCR methods, using a T7 promoter-controlled in vitro RNA transcription system as previously described[33] (Table 1). All the CTP and UTP used for synthesis of the pRNA nanoparticles were 2'-fluoro modified, except the control unmodified pRNA nanoparticles used in the stability assays. Following an overnight transcription at 37° C., RNA strands were purified using RNA clean and concentrator kits (ZYMO research) and examined by 8 M urea denatured 8% PAGE gel. pRNA nanoparticles were assembled by mixing the equal molar amounts of p1 and p2 strands and gradually annealing from 90° C. to 20° C. in 1×RNA annealing buffer containing 50 mM Tris-HCl (pH 7.5), 50 mM NaCl and 1 mM EDTA on a PCR machine. The generated pRNA nanoparticles were examined by 8% native PAGE gels as previously described.[33] To generate AF647-conjugated pRNA nanoparticles, a 5'-termial AF647-conjugated RNA strand was synthesized (TriLink) for annealing.

Characterization of pRNA nanoparticles. The hydrodynamic diameter and Tm value of pRNA nanoparticles were determined using dynamic light scattering and TGGE assay, respectively, as previously described.[54] The AFM imaging of the pRNA nanoparticles was performed at the University of Nebraska Medical Center imaging facility as previously reported.[55] Briefly, the pRNA nanoparticles (5 µL) were deposited on APS modified mica [56] for a total of 2 min of incubation time. Excess samples were washed with DI water and dried under a flow of Argon gas. AFM images in air were acquired using MultiMode AFM NanoScope IV system (Bruker Instruments) operating in tapping mode with 1.5 Hz scanning rate. TESPA probes from Bruker were used for tapping mode imaging. The probe had a spring constant of about 40 N/m and a resonance frequency between 320 kHz. For stability analyses, the pRNA nanoparticles were treated with RNase A, 8 M urea, or 10% FBS supplemented DMEM medium at 37° C., respectively. The integrity of the pRNA nanoparticles was examined through native PAGE gel electrophoresis.

pRNA nanoparticle cellular uptake assay. BT474 and MDA-MB-231 cells were seeded into 4-well Lab-Tek chamber slides (Nalge Nunc international, Thermo scientific) and incubated with 10 µg/mL AF647-conjugated pRNAs at 4° C. for 30 min. After washing with PBS for three times, cells were incubated at 37° C. for another hour. Cells were then fixed with 4% formaldehyde, permeated with 0.25% Trinton X-100, and stained with FITC-conjugated β-actin antibody (Sigma) and DAPI (Sigma). pRNA nanoparticle uptake was examined using a laser scanning confocal microscope (Zeiss). For flow cytometry analyses, BT474 cells were incubated with AF647-labeled pRNA nanoparticles at 37° C. for 3 h. After washing three times with PBS, the cellular uptake of pRNAs was determined using a BD LSRFortessa™ flow cytometer.

Real-time PCR. Total RNA was extracted from cultured cells using an RNeasy mini kit (Qiagen), or from tumor tissues by Trizol reagent (Invitrogen), according to the manufacturer's instructions, followed by reverse-transcription using Superscript IV reverse transcriptase (Invitrogen). Real-time PCR was performed using fast start SYBR master mix (Roche) in a 7900HT Fast Real-time system (Applied Biosystem). The expression of MED 1, TFF1, c-Myc, cyclinD1 and MMP-9 was analyzed using GAPDH as the internal reference.

Western blot analyses. Cells were lysed in RIPA buffer supplemented with cocktail protease inhibitors (Roche) and PMSF, and subjected to SDS-PAGE gel electrophoresis. After transferring to nitrocellulose membranes, immunoblotting was performed by incubation with anti-MED1 and anti-βactin primary antibodies, followed by horseradish peroxidase-coupled goat anti-rabbit secondary antibody (Jackson ImmunoResearch) treatment and visualization with an enhanced chemiluminescence system (Pierce).

MTT assay. BT474 cells were treated with pRNAs alone or together with 4-hydroxy-tamoxifen (Sigma) for 48 h. After the treatment, 10 µL MTT reagent ((3-(4,5-Dimethylthiazol-2-yl)-2,5-diphenyltetrazolium bromide, Sigma) were added to cell culture medium and incubated at 37° C. for 4 h. The formazan crystals were dissolved in DMSO, and the absorbance of the solution at 570 nm ($A_{570nm}$) was determined using a multifunctional microplate reader (BioTek).

Migration and metastasis assay. The 8-µm-pore-size polycarbonate membrane, which separates the two chambers of a 6.5-mm Transwell (Costar), was coated with or without 1:8 DMEM-diluted Matrigel (Corning). Transwell assay was performed as previously described.[57] Briefly, BT474 cells were treated with pRNAs alone or together with 4-hydroxy-tamoxifen (4-OHT) for 48 h and starved with serum-free DMEM containing 0.2% BSA overnight. On the next day, cells were collected and $2 \times 10^5$ cells were seeded to the upper chamber of Transwell. The lower chamber was filled with 600 µL DMEM medium containing 10% FBS. After incubation at 37° C. for 24 h, cells on the membranes were fixed and stained with 0.1% crystal violet in 20% ethanol solution. Cells at top side of membranes were removed completely, and cells at the bottom side were examined with an Olympus SZX12 microscope and counted.

Mammosphere culture and breast cancer stem cell analyses. BT474 cells were treated with pRNAs for 48 h. Then, cells were suspended in DMEM/F12 medium supplemented with 1×B27 (Thermo Fisher), 20 ng/mL bFGF and 20 ng/mL EGF (R&D), and added into 24-well ultralow attachment plates. After treatment with or without 1 µM 4-OHT for 7 days, mammosphere formation was recorded using an Axiovert S100 TV inverted microscope (Zeiss). Xenograft tumor tissues were cut into small pieces and digested with trypsin and collagenase at 37° C. for 1 h, and tumor cells were collected and rinsed with pre-cold PBS. All cells were stained with FITC-conjugated anti-CD44 antibody and PE-conjugated anti-CD24 antibody (BD Pharmingen) in the dark on ice for 30 min. After resuspension with 0.5 mL PBS buffer, $CD44^+$/$CD24^{-/low}$ cell population was analyzed by flow cytometry.

Orthotopic xenograft breast tumor mouse model, in vivo imaging and anti-tumor therapy. Six-week-old female athymic nude mice were purchased from Charles River Laboratories, and all animal procedures were performed under IACUC-approved protocols at the University of Cincinnati. Athymic nude mice were orthotopically injected with $1 \times 10^7$ BT474-luc cells mixed with matrigel into the fat pads of the forth pair of mammary glands. When the tumor sizes reached 100-150 mm³, the mice were randomly divided into four groups (4/group) and intravenously (i.v.) injected with pRNAs (4 mg/Kg) once a week for three weeks. For tamoxifen treatments, 0.5 mg tamoxifen (Sigma) dissolved in sesame oil was intraperitoneally (i.p.) injected into mice 5 days a week for three weeks. The tumor volume was monitored every 3 days, and tumor size was calculated using the formula: volume=$0.5 \times (width)^2 \times (length)$. For in vivo pRNA nanoparticle targeting and tumor imaging, mice were i.v. injected with AF647-conjugated pRNA nanoparticles or i.p. injected with D-luciferin and imaged using the IVIS Lumina imaging system with Living Images 3.0 software (Caliper Life Sciences). At the end of the treatment, mice were sacrificed and the organs including heart, liver, spleen, lung, kidneys and tumors were also excised for imaging. After the tumor weights were recorded, part of the tumor tissues were digested with trypsin and collagenase, lysed for extraction of total proteins and RNAs, or fixed in 10% neutral buffered formalin along with organ tissues, respectively, for further western blot, real-time PCR and IHC studies, etc. To examine the bio-distribution of pRNA nanoparticles within the tumor issues, O.C.T.-embedded frozen sections (5 µm) were examined by confocal microscopy. Same frozen sections were also stained with anti-CD31 primary antibody (BD Biosciences) and Alexa488-conjugated secondary antibody for blood vessels.

H&E and Immunohistochemical (IHC) staining. The mice organs (heart, liver, spleen, lung and kidney) and tumors were collected and fixed in 10% neutral buffered formalin, followed by dehydration by gradient series of ethanol (75%, 85%, 95% and 100%). The dehydrated tissues were embedded in paraffin and cut into 5 µm sections. For H&E staining, the tissue sections were sequentially stained with hematoxylin and eosin (Sigma) and assessed for histology. To examine the MED1 and Ki-67 expression in tumor tissues, IHC staining was performed as previously described.[14] Briefly, tumor tissue sections were first deparaffinized and heat-induced antigen retrieval was performed using citrate buffer before incubation with anti-MED1 or anti-Ki-67 primary antibodies (Thermo scientific) at 4° C. overnight. Then, the sections were incubated with biotin-SP-conjugated secondary antibody (Jackson ImmunoResearch), and developed using Vectastain ABC kit with DAB substrates (Vector Lab). The nuclei were counterstained with hematoxylin. Finally, the sections were dehydrated and mounted with neutral balsam. The images were analyzed via an Axioplan Imaging 2e microscope (Zeiss).

Statistics. Data were represented as mean±SEM from at least three independent experiments. The differences among groups were calculated using Student's t-test or one-way ANOVA analysis followed by Tukey's post test (GraphPad Prism, GraphPad Software).

Example 1

This example illustrates generation and characterization of 3-WJ pRNA-HER2apt-siMED1 nanoparticles.

Figure 7A:
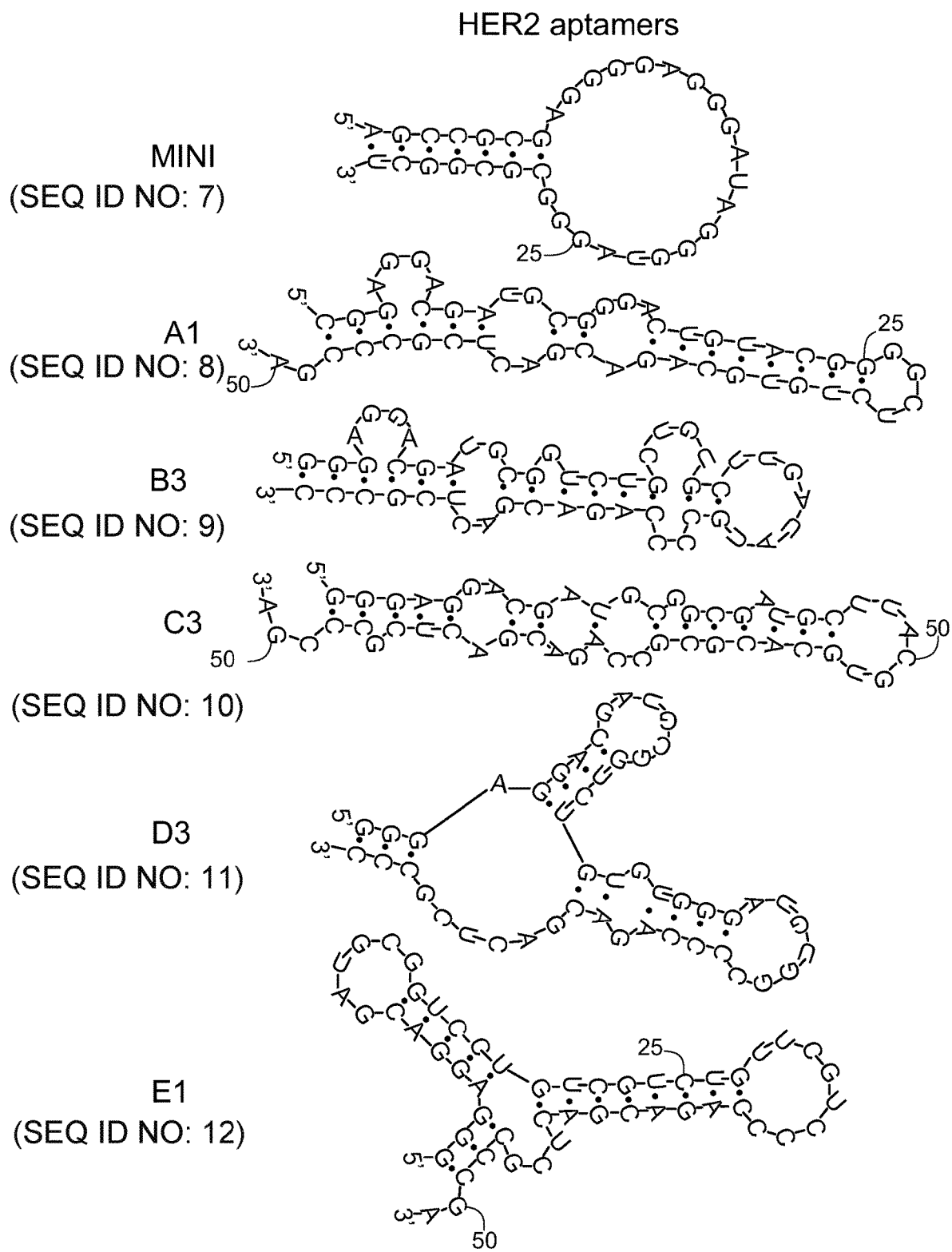
Figure 7B:
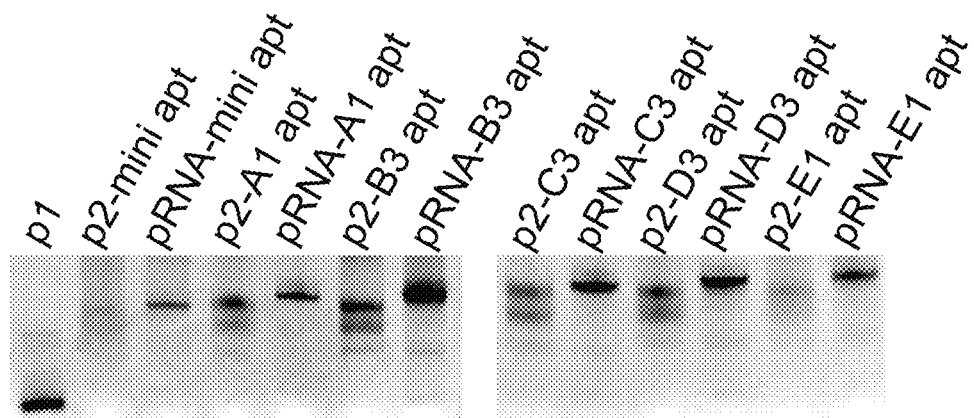
Figure 7C:
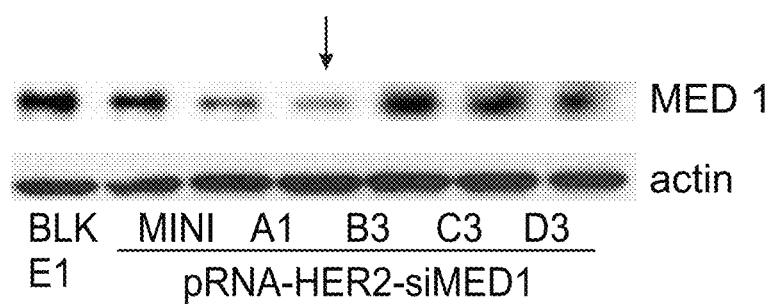

Utilizing the three-way junction (3-WJ) of Phi29 pRNA as the core unit, self-assembled double-strand pRNA nanoparticle bearing a HER2-targeting RNA aptamer and two different MED1 siRNAs for in vitro and in vivo delivery were assembled (termed pRNA-HER2apt-siMED1, FIG. 1A). In search for a HER2 aptamer suitable to deliver pRNA-HER2apt-siMED1 into HER2-overexpressing breast cancer cells, several published HER2 RNA aptamers [31,32] were tested (FIGS. 7A and 7B) and it was found that the B3 aptamer could target HER2-overexpressing BT474 cells and knockdown MED1 expression with the highest efficiency (FIG. 7C).

Figures 1B, 1C:
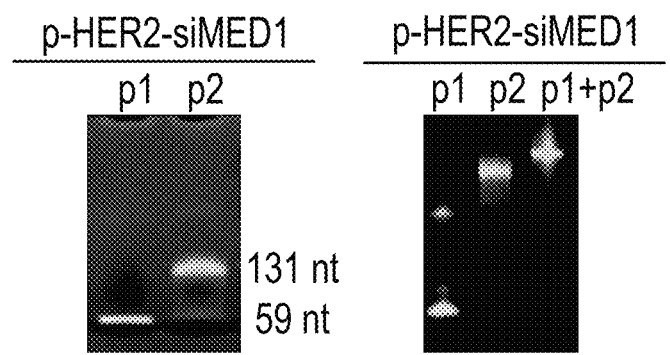
Figure 1D:
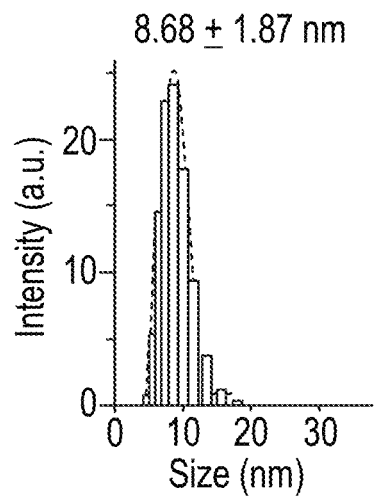
Figure 1E:
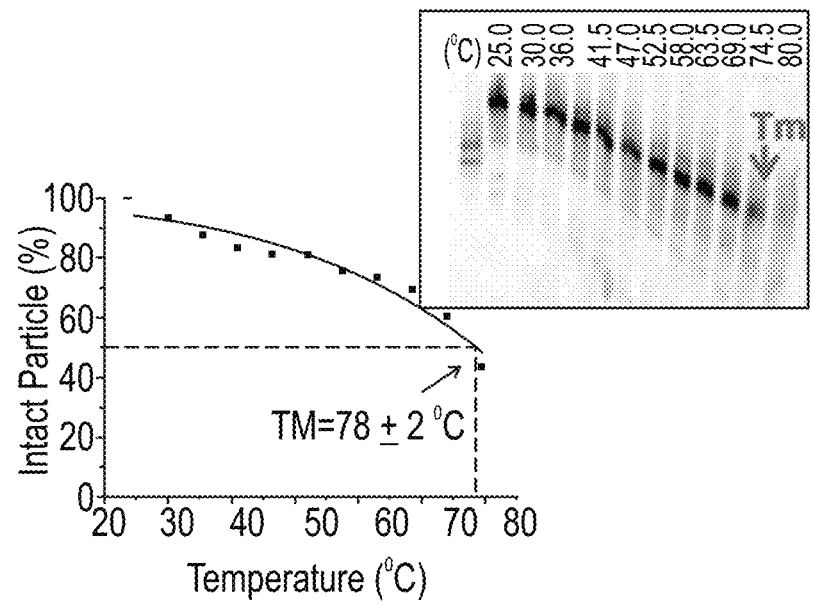
Figure 1F:
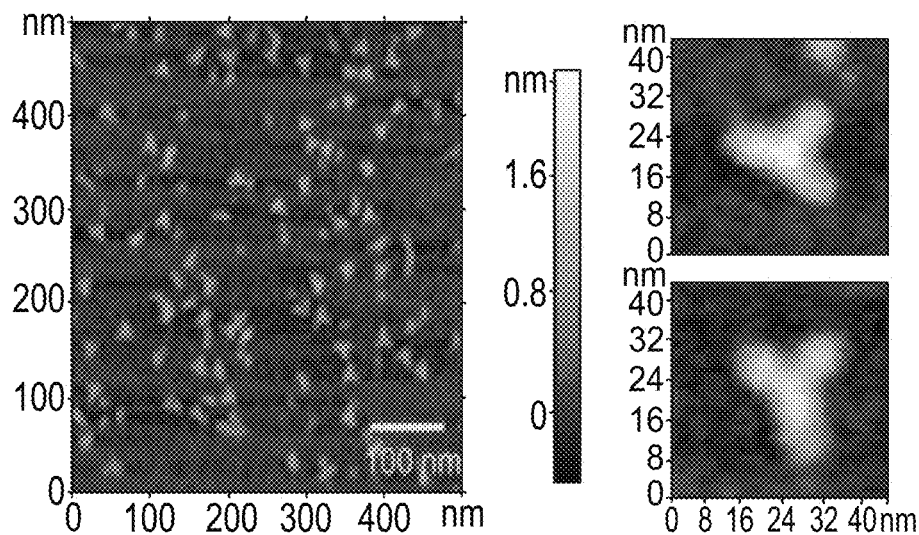

To construct pRNA-HER2apt-siMED1 and control nanoparticles, two strands, p1 and p2, were transcribed from the DNA templates using an in vitro T7 promoter-controlled RNA transcription system (FIG. 1B, Table 1) (see Shu, Y. et al. *Nat. Protoc.* 2013, 8, 1635-1659, incorporated herein by reference). These two strands were then mixed in equal molar ratio and annealed to generate uniform pRNA nanoparticles (FIG. 1C). The hydrodynamic size of the pRNA nanoparticles was determined to be 8.68 ±1.87 nm by dynamic light scattering (DLS) measurements (FIG. 1D). The Tm value was determined to be 78±2° C. by temperature gradient gel electrophoresis (TGGE) assay (FIG. 1E). And the atomic force microscopy (AFM) images clearly demonstrated the formation of homogenous three-way junction architecture of the pRNA nanoparticles as previously described [28] (FIG. 1F).

Figure 1G:
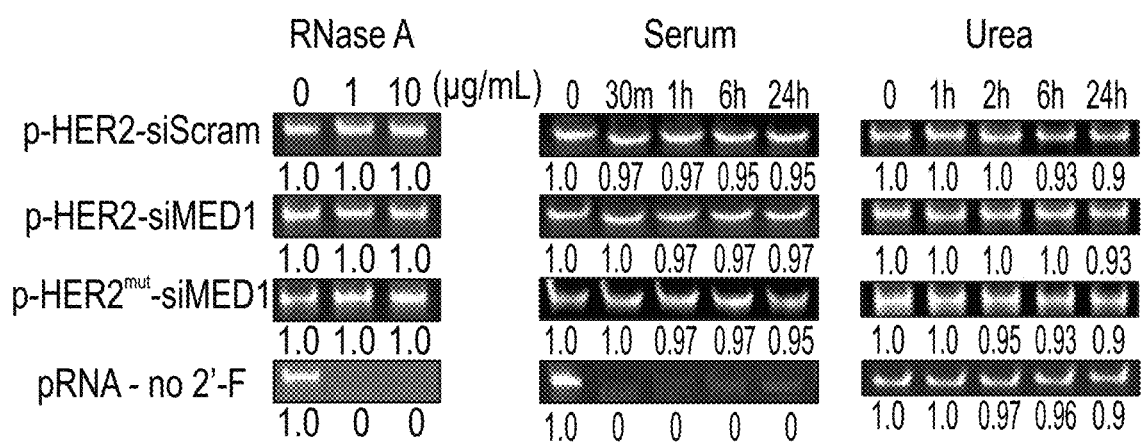
Figure 2A:
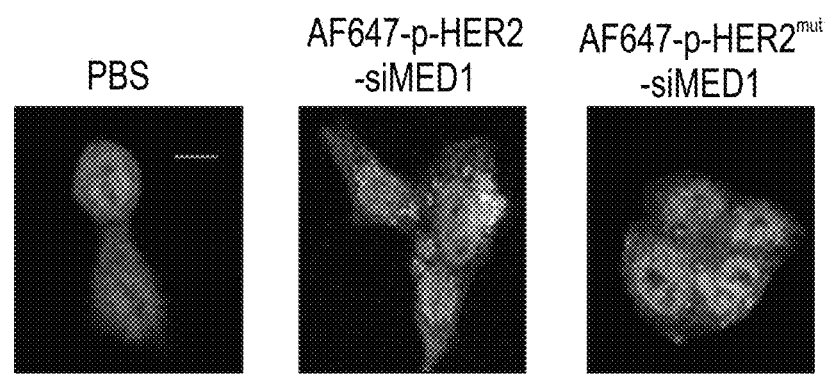
FIGS. 2A-2F. Evidence pRNA-HER2apt-siMED1 nanoparticles specifically targeted BT474 cells in vitro and in vivo.
Figure 2B:
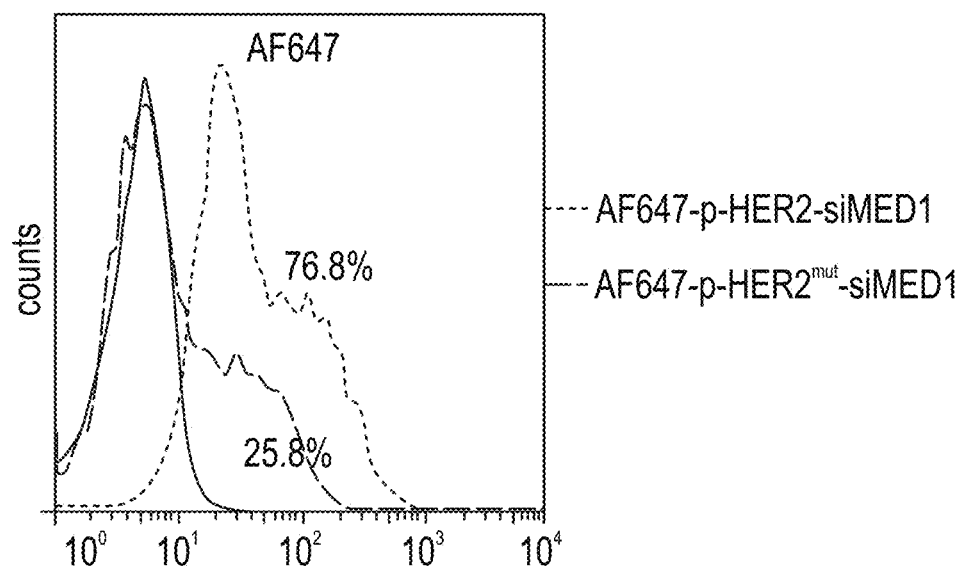

As shown in FIG. 1G, the 2'-F-modified but not unmodified pRNA nanoparticles were resistant to 10 μg/mL RNase A treatment and were highly stable in 10% FBS-supplemented DMEM medium at 37° C. Interestingly, both modified and unmodified pRNA nanoparticles maintained their structure in 8M urea, reflecting the highly stable nature of the three-way junction. Next, the pRNA nanoparticles were digested with recombinant Dicer enzyme (Genlantis) [34] to confirm the release of siRNAs as indicated by the generation of 21-23 bp small RNAs after digestion (FIG. 7D). Taken together, these results indicated that the self-assembled pRNA-HER2apt-siMED1 nanoparticles formed uniformly-sized ultra-compact and stable structures capable of releasing siRNAs.

the uptake efficiency (FIG. 2B and FIG. 8D). Together, these results demonstrated the specific and efficient targeting of pRNA-HER2apt-siMED1 nanoparticles into HER2-overexpressing breast cancer cells.

Figure 2C:
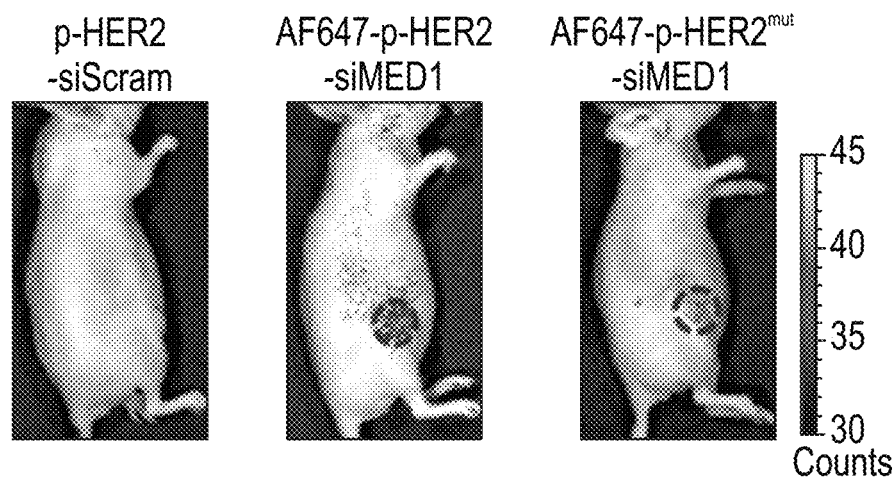
Figure 2D:
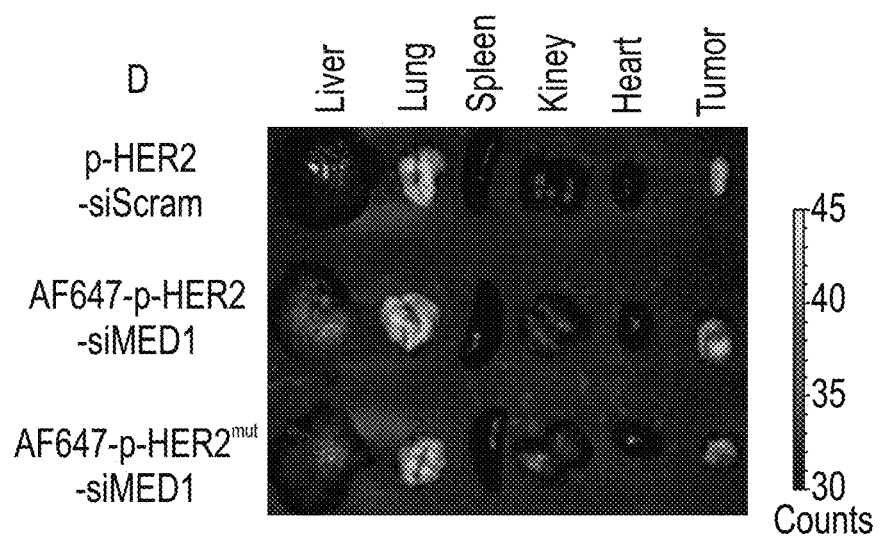

To examine the in vivo siRNA delivery effects of pRNA-HER2apt-siMED1 nanoparticles, an orthotopic xenograft mouse model was adapted/utilized by implanting luciferase-overexpressing BT474 cells into the forth mammary fat pad of the nude mice. The overexpression of HER2 in both BT474 cells and xenograft tumors was confirmed by western blot analyses (FIG. 8A and FIG. 8E). The live animal imaging demonstrated that AF647-conjugated pRNA-HER2apt-siMED1 nanoparticles but not HER2 aptamer mutant nanoparticles were strongly accumulated in the area of the xenograft tumor after systemic administration (FIG. 2C). Further in vivo biodistribution analyses confirmed the predominant accumulation of wild type but not HER2-mutant aptamer-containing nanoparticles in the xenograft tumors while similar low levels of residual signals were detected in liver and kidney in both groups (FIG. 2D). Importantly, confocal microscopic analyses of frozen tumor sections indicated that pRNA-HER2apt-siMED1 nanopar-

TABLE 1

Sequences used for construction of specific exemplary pRNA nanoparticles

5'-3'

| | | |
|---|---|---|
| pRNA-HER2apt-siScram | p1 | GGAucAcGcuucAuAuAcAAAGGAucAAucAuGGccAAucuuAuuucGcccAuGAccuu* (SEQ ID NO: 1) |
| | p2 | GGucAuGGGcGAAAuAAGAAAGGccAuGuGuAuGuGGGGGGAGGAcGAuGcGGucuGcuG uGcuuGAuAuGccccAGAcGAcucGcccccccAcAuAcuuuGuuGAuccAAuGuAuAuGAA GcGuGAuccuu (SEQ ID NO: 2) |
| pRNA-HER2apt-siMED1 | p1 | GGAcAGuGAAAGuGAGucAAAGGAucAAucAuGGccAAAGAuGuuAcuuuGAGAGccuu (SEQ ID NO: 3) |
| | p2 | GGcucucAAAGuAAcAucuAAGGccAuGuGuAuGuGGGGGGAGGAcGAuGcGGucuGcuG uGcuuGAuAuGccccAGAcGAcucGcccccccAcAuAcuuuGuuGAuccAAuGAcucAcuu ucAcuGuccuu (SEQ ID NO: 4) |
| pRNA-HER2apt^mut-siMED1 | p1 | GGAcAGuGAAAGuGAGucAAAGGAucAAucAuGGccAAAGAuGuuAcuuuGAGAGccuu (SEQ ID NO: 5) |
| | p2 | GGcucucAAAGuAAcAucuAAGGccAuGuGuAuGuGGGAuGAGGAGuAuGAAGAuAccuG uAcuuGAuAuGccccAGAcGAcAuucccccccAcAuAcuuuGuuGAuccAAuGAcucAcuu ucAcuGuccuu (SEQ ID NO: 6) |

*The lower letters indicated 2'-Fluoro modified nucleotides.
**Mutations of HER2 aptamers are indicated as Bold.

Example 2

This example illustrates specific targeting of HER2-overexpressing breast cancer cells by pRNA-HER2apt-siMED1 nanoparticles in vitro and in vivo.

Figure 2E:
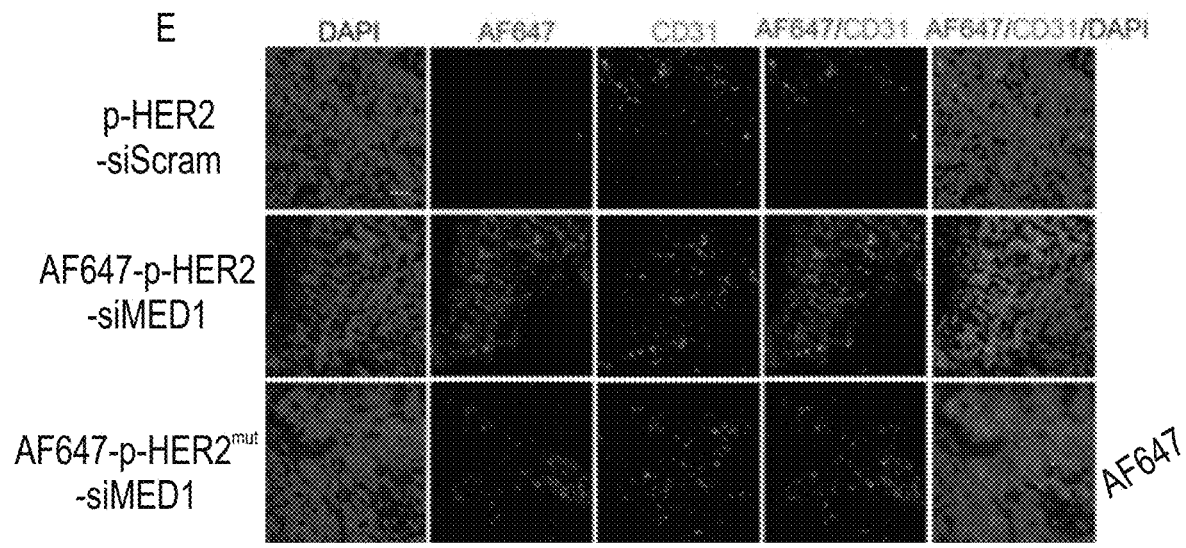
Figure 2F:
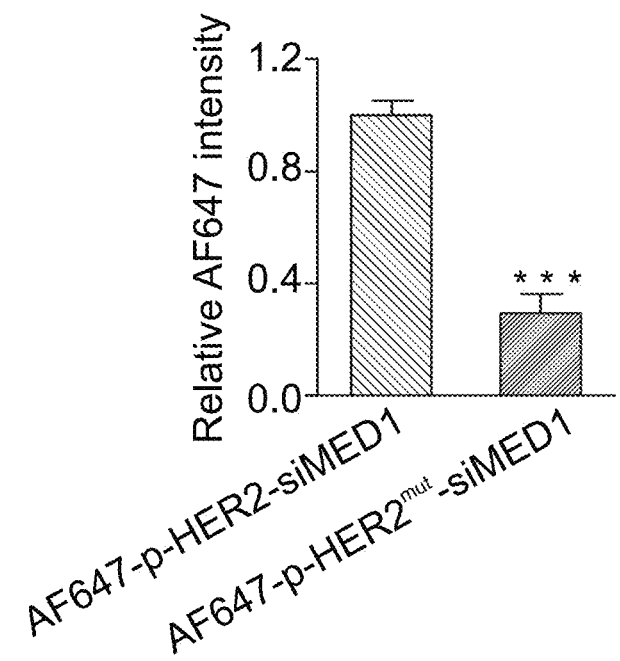

Next, the targeting capabilities of the AlexaFluor 647 (AF647)-conjugated pRNA-HER2apt-siMED1 nanoparticles using HER2-overexpressing BT474 cells and control MDA-MB-231 cells were examined (FIG. 8A).[35] It was found that pRNA-HER2apt-siMED1 nanoparticles can bind and be readily internalized into BT474 but not MDA-MB-231 cells (FIGS. 8B, 8C, FIG. 2A). However, mutating the HER2 aptamer in the stem region dramatically impaired the binding and internalization of the pRNA-HER2apt-siMED1 nanoparticles (FIG. 8B, FIG. 2A). Moreover, flow cytometric analyses further determined that pRNA-HER2apt-siMED1 nanoparticles were effectively taken up by BT474 cells rather than MDA-MB-231 cells after 3 h incubation at 37° C., whereas HER2 aptamer mutation notably decreased ticles very effectively penetrated to tumor cells while a majority of HER2 aptamer mutant nanoparticles remained in the microvessels (stained with an anti-CD31 antibody) as indicated by their localizations (FIGS. 2E and 2F). These results indicated that pRNA-HER2apt-siMED1 nanoparticles could specifically target HER2-overexpressing breast cancer both in vitro and in orthotopic xenograft mouse models.

Example 3

This example demonstrates inhibition of cell growth and metastatic capabilities of HER2-overexpressing breast cancer cells by pRNA-HER2apt-siMED1 nanoparticles in vitro.

Figure 3A:
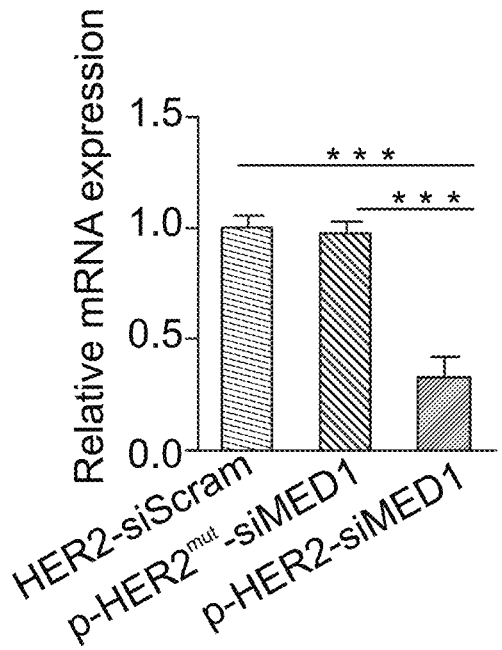
FIGS. 3A-3H. Collectively demonstrate that pRNA-HER2apt-siMED1 nanoparticles silenced MED1 expression and inhibited the cell growth and metastatic capabilities of HER2-positive breast cancer cells in vitro.
Figure 3B:
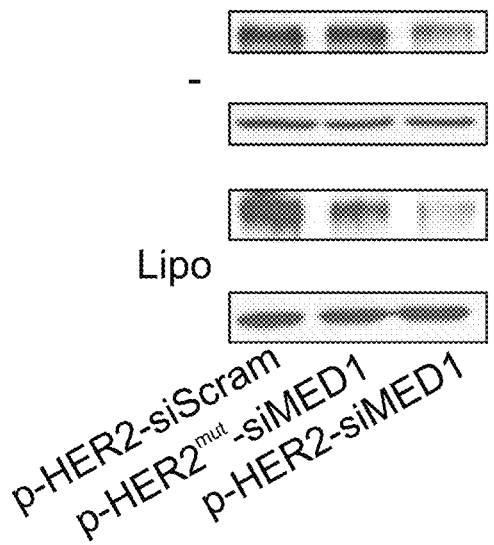
Figure 9A:
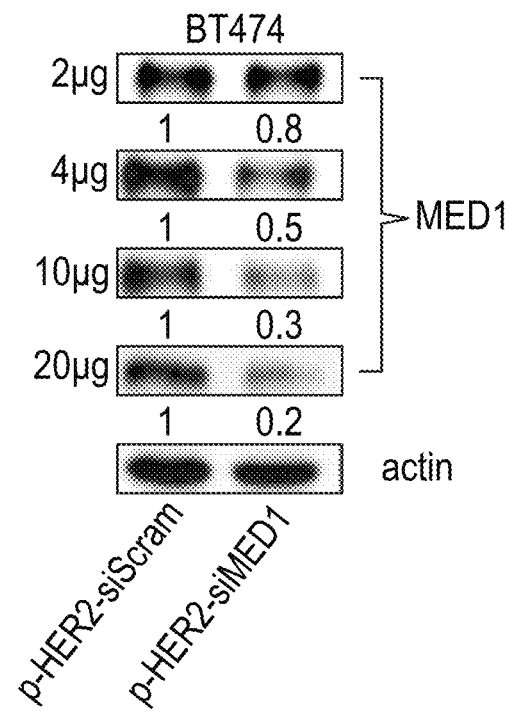
FIGS. 9A-9B. Evidence that pRNA-HER2apt-siMED1 nanoparticles dose-dependently knockdown MED1 expression and inhibited the growth of BT474 cells.
Figure 10A:
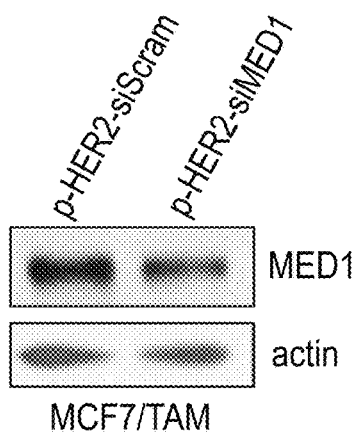
FIGS. 10A-10D. Evidence that pRNA-HER2apt-siMED1 nanoparticles silenced MED1 expression and sensitized two other HER2+ breast cancer cells to tamoxifen treatment.
Figure 10B:
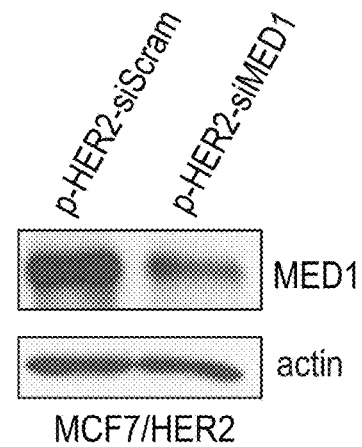

Next, the ability of pRNA-HER2apt-siMED1 nanoparticles to silence the expression of MED1 in BT474 and MDA-MB-231 human breast cancer cells was examined. Using real-time PCR analyses, a significant depletion of nearly 70% of MED1 mRNA in BT474 cells after pRNA- HER2apt-siMED1 but not pRNA-HER2apt$^{mut}$-siMED1 treatment was found (FIG. 3A). Western blots further confirmed that MED1 protein level was greatly reduced by pRNA-HER2apt-siMED1treatment in BT474 cells but not in MDA-MB-231 cells (FIG. 3B and FIG. 8F, up panel). As controls, transfection of wild type and mutant HER2 aptamer containing-nanoparticles with lipofectamine 2000 resulted in MED1 silencing in both BT474 and MDA-MB-231 cells (FIG. 3B and FIG. 8F, bottom). Moreover, the pRNA-HER2apt-siMED1 nanoparticles decreased MED1 protein level in BT474 cells in a dose-dependent manner (FIG. 9A). In addition, the effect of pRNA-HER2apt-siMED1 treatment on MED1 silencing in two other HER2-overexpressing and tamoxifen resistant breast cancer cell lines MCF-7/HER2 and MCF-7/TAM, respectively were confirmed (FIGS. 10A and 10B).[36,37] These data demonstrate that the pRNA-HER2apt-siMED1 nanoparticles specifically and efficiently silence MED1 expression in HER2-overexpressing breast cancer cells.

Figure 3C:
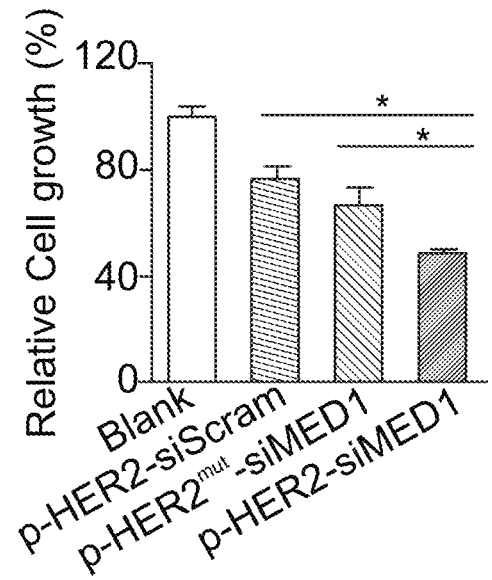
Figure 3D:
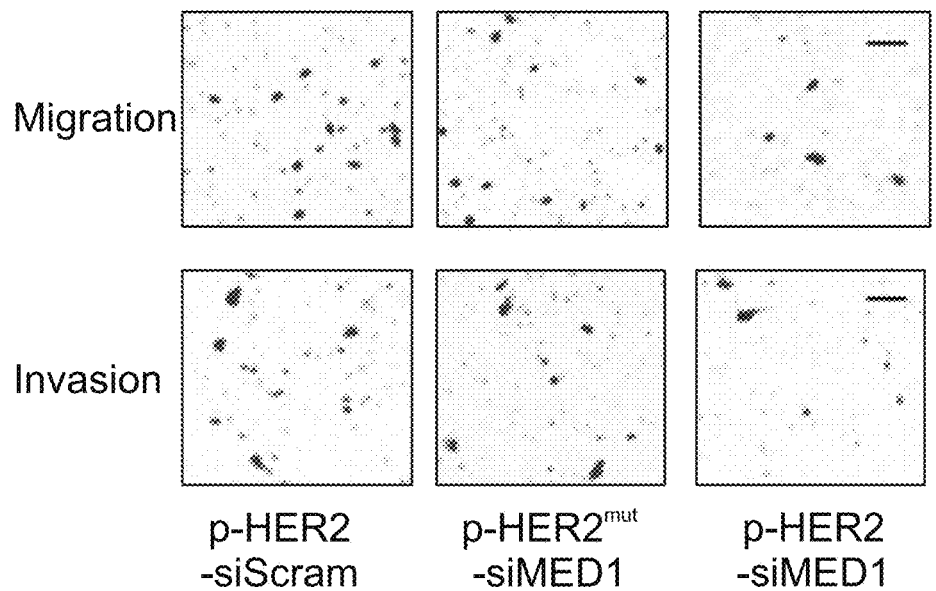
Figure 3E:
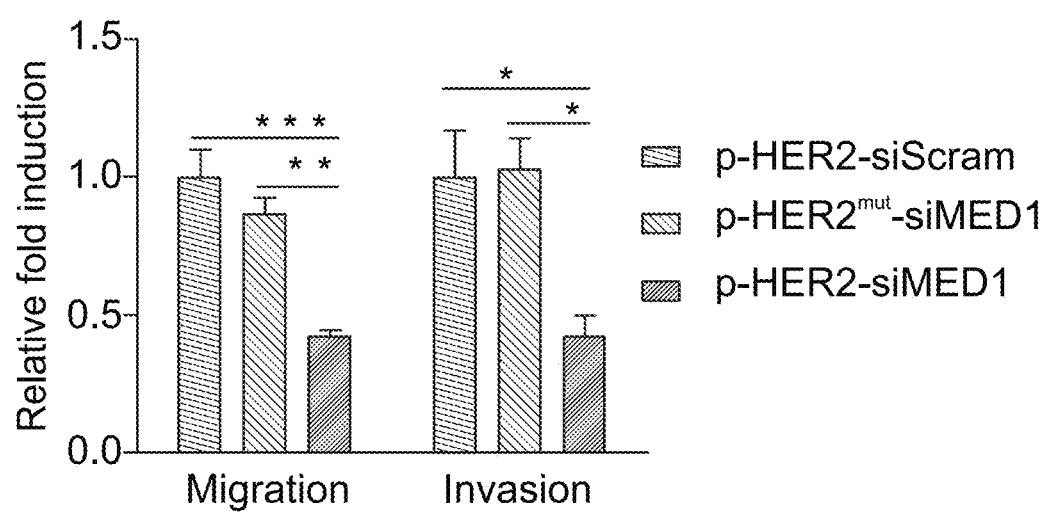
Figure 3F:
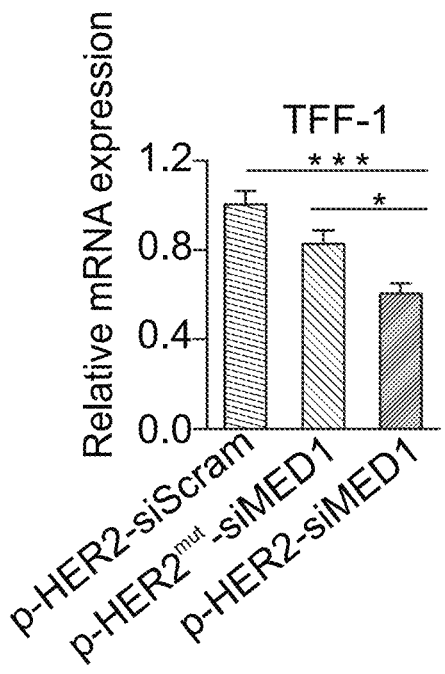
Figure 3G:
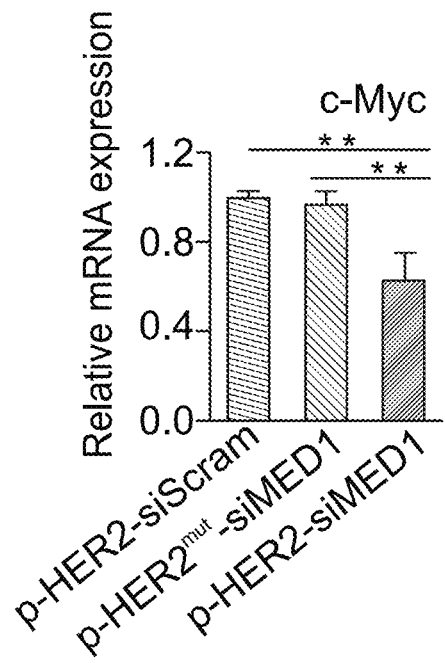
Figure 3H:
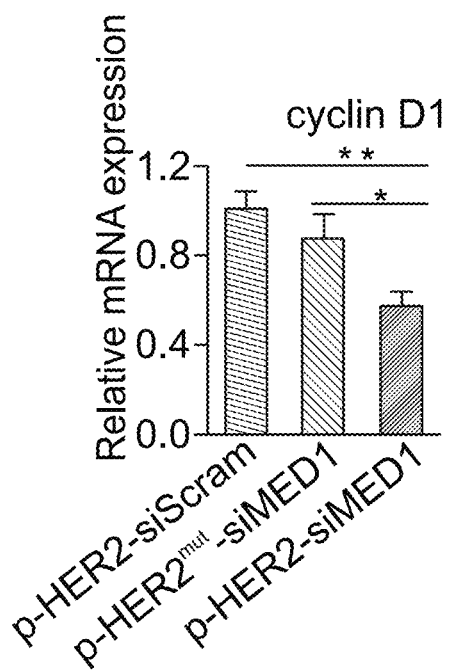
Figure 9B:
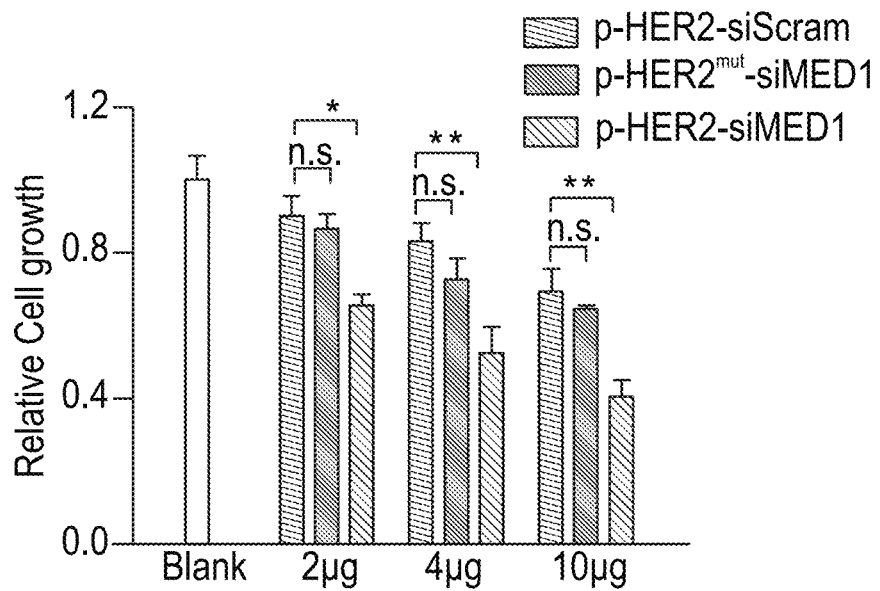

As MED1 plays a key role in ERα-dependent growth and metastasis of HER2-overexpressing breast cancer, the effect of pRNA-HER2apt-siMED1 nanoparticles on BT474 cell growth and metastatic capabilities was further examined. As shown by MTT assay, the cell growth was dose-dependently inhibited by pRNA-HER2apt-siMED1 but not pRNA-HER2apt$^{mut}$-siMED1 treatment (FIG. 3C and FIG. 9B). Furthermore, transwell assays indicated that both migration and invasion abilities of BT474 cells were specifically suppressed by the treatment of pRNA-HER2apt-siMED1 but not pRNA-HER2apt$^{mut}$-siMED1 nanoparticles (FIGS. 3D and 3E). Next, the mRNA expression levels of ERα-dependent genes using real-time PCR analyses was examined and the expression of well-known ERα/MED1 target genes including TFF-1, c-Myc and cyclin D1 were found to be all significantly down-regulated after pRNA-HER2apt-siMED1 treatment [38] (FIGS. 3F-3H). Taken together, these data supported that pRNA-HER2apt-siMED1 nanoparticles could inhibit cell growth and metastatic capabilities of HER2-overexpressing breast cancer cells through silencing MED1 and its downstream gene expression.

Example 4

This example illustrates sensitizing HER2-overexpressing breast cancer cells to tamoxifen treatment both in vitro and in vivo by the bio-safe-pRNA-HER2apt-siMED1 nanoparticles.

Figure 4A:
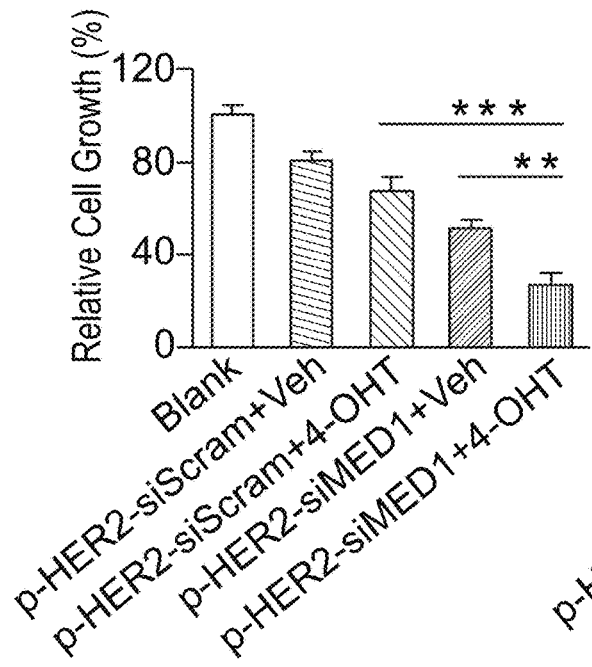
FIGS. 4A-4F. Evidence that pRNA-HER2apt-siMED1 nanoparticles sensitized HER2-overexpressing BT474 cells to tamoxifen treatment.
Figure 4B:
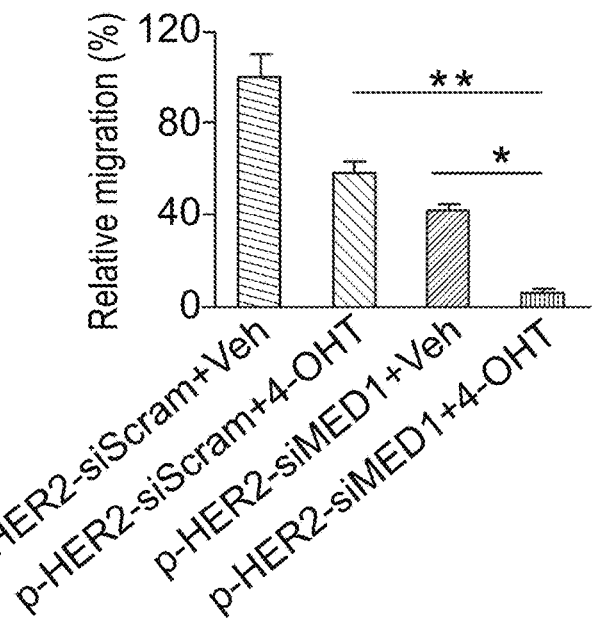
Figure 4C:
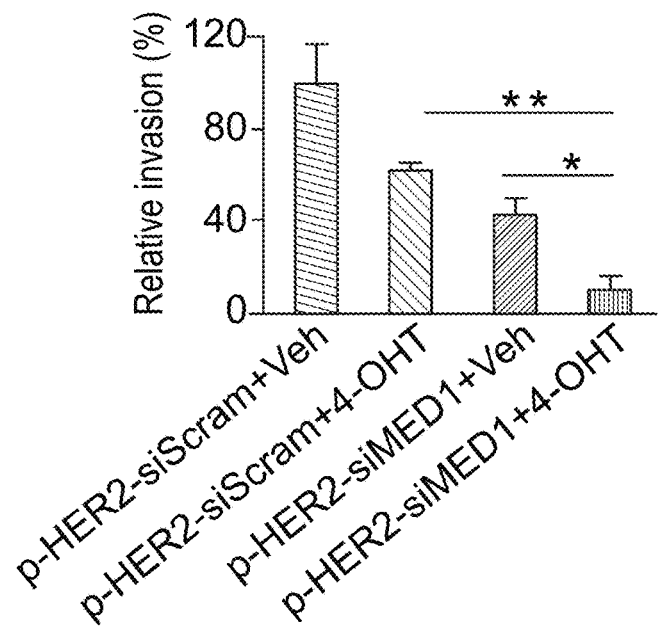
Figure 4D:
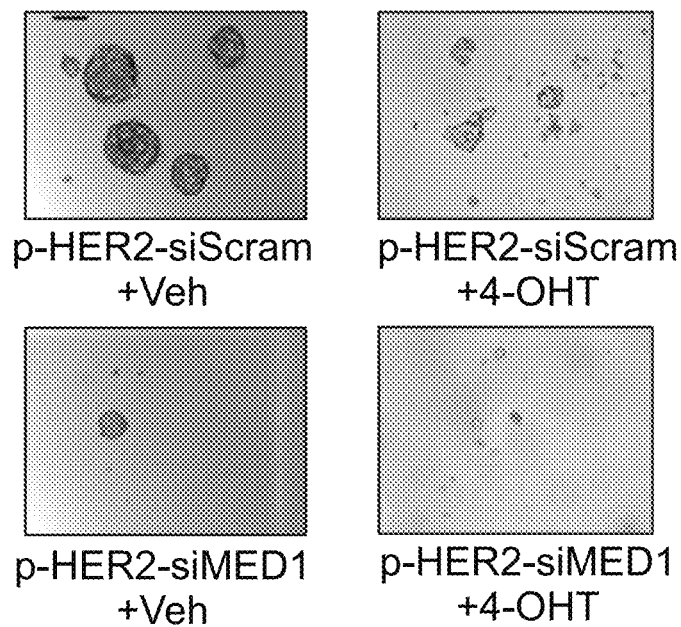
Figure 4E:
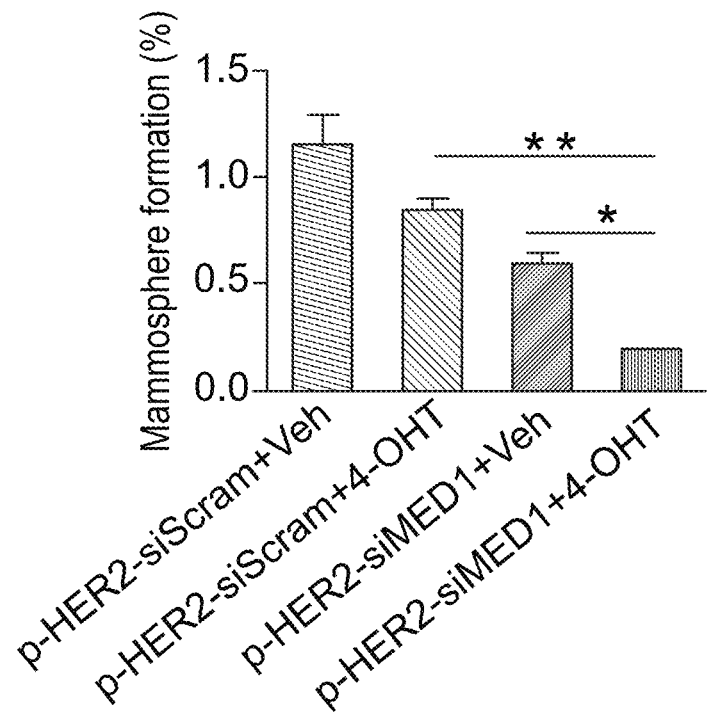
Figure 4F:
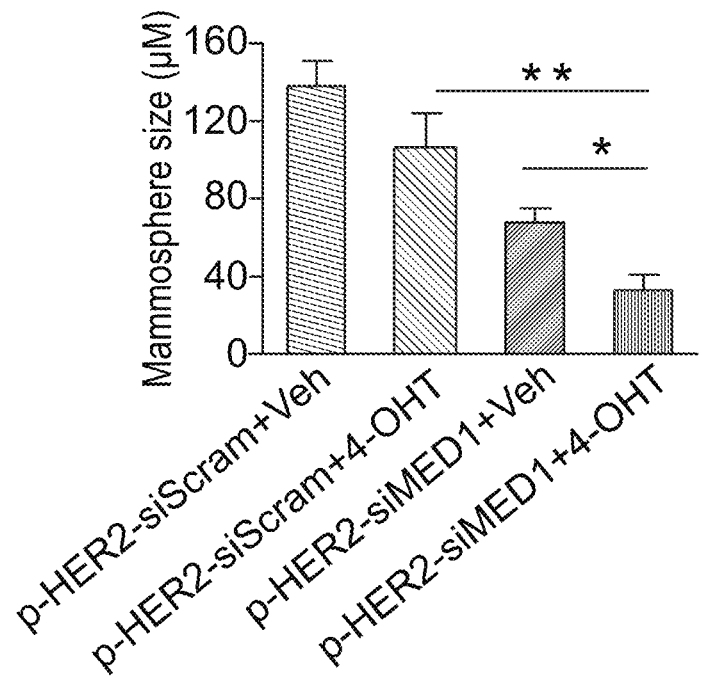
Figure 10C:
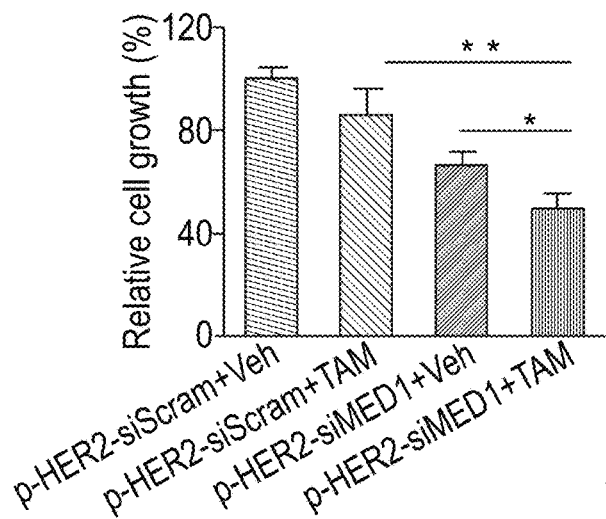
Figure 10D:
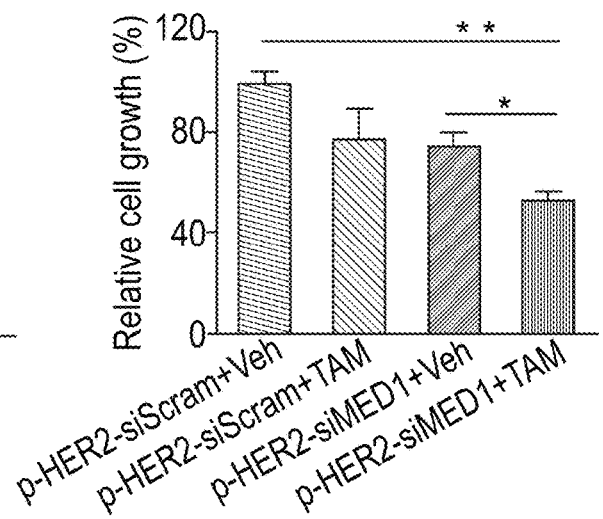
Figure 11:
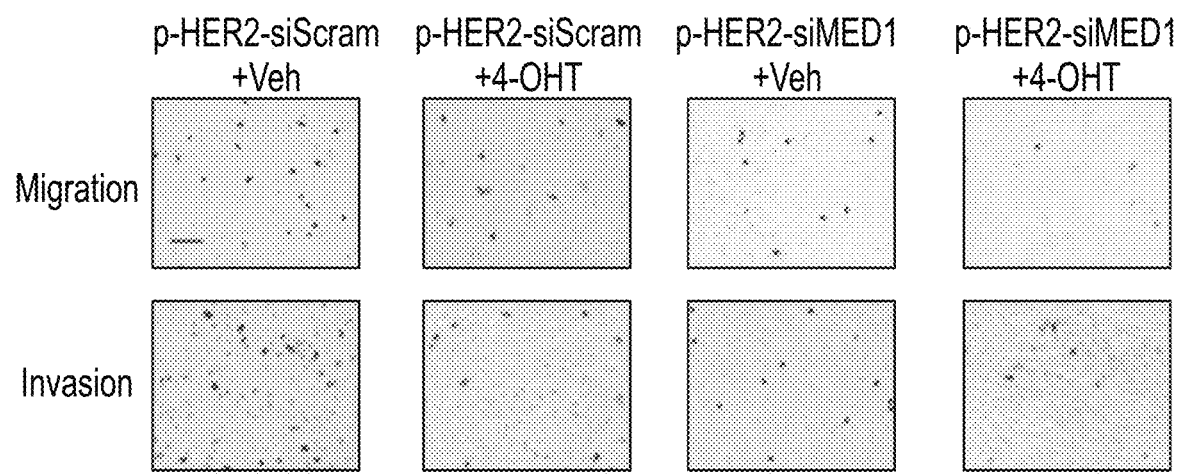
FIG. 11. Demonstrates that pRNA-HER2apt-siMED1 nanoparticles strongly inhibited the migration and metastasis of BT474 cells in combination with tamoxifen treatment. BT474 cells were treated with pRNA nanoparticles alone or together with 1 μM 4-hydroxy-tamoxifen (4-OHT) for 48 h. Cell migration and invasion were then examined using transwell assay. Photos were recorded using an Olympus SZX12 microscope. Scale bar: 100 μm.

Since MED1 has recently been reported to play key roles in tamoxifen resistance of human breast cancer, the combinational effects of pRNA-HER2apt-siMED1 nanoparticles with tamoxifen on the growth and metastatic potential of BT474 cells was examined. The results showed that the pRNA-HER2apt-siMED1 nanoparticles significantly enhanced the inhibitory effects of tamoxifen not only on the growth but also the migration and invasion capabilities of BT474 cells (FIGS. 4A-C and FIG. 11). The combinational effect of pRNA-HER2apt-siMED1 nanoparticles with tamoxifen treatment on two other HER2-overexpressing breast cancer cells MCF-7/HER2 and MCF-7/TAM were also confirmed (FIGS. 10C-D). Moreover, the effect of pRNA-HER2apt-siMED1 and its combination with tamoxifen on breast cancer stem cells using an in vitro mammosphere culture assay was examined[39] and it was discovered that pRNA-HER2apt-siMED1 alone and in combination with tamoxifen not only greatly reduced the number of mammosphere formation but also the size of these mammospheres (FIGS. 4D-F).

Figure 5A:
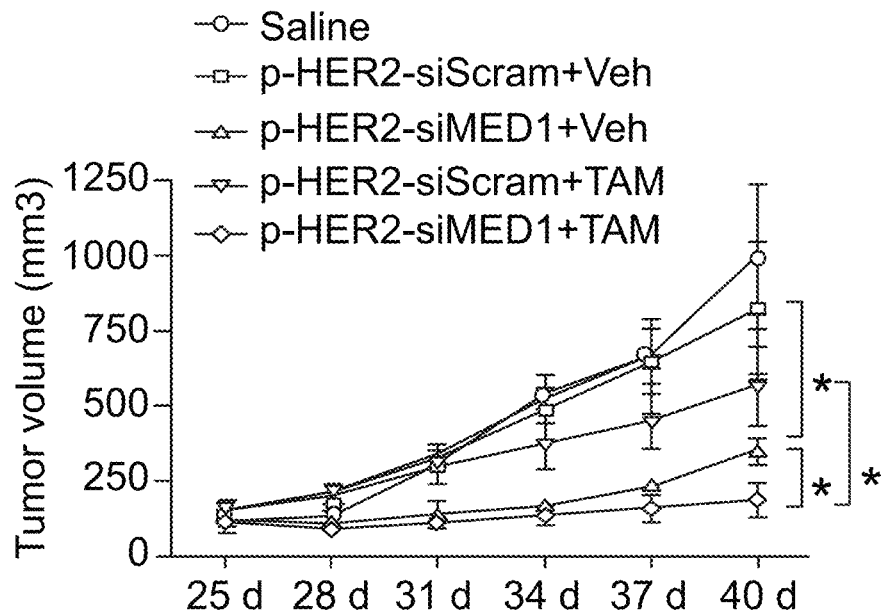
FIGS. 5A-5I. Show that pRNA-HER2apt-siMED1 nanoparticles inhibited HER2-overexpressing breast tumor growth in vivo.
Figure 5B:
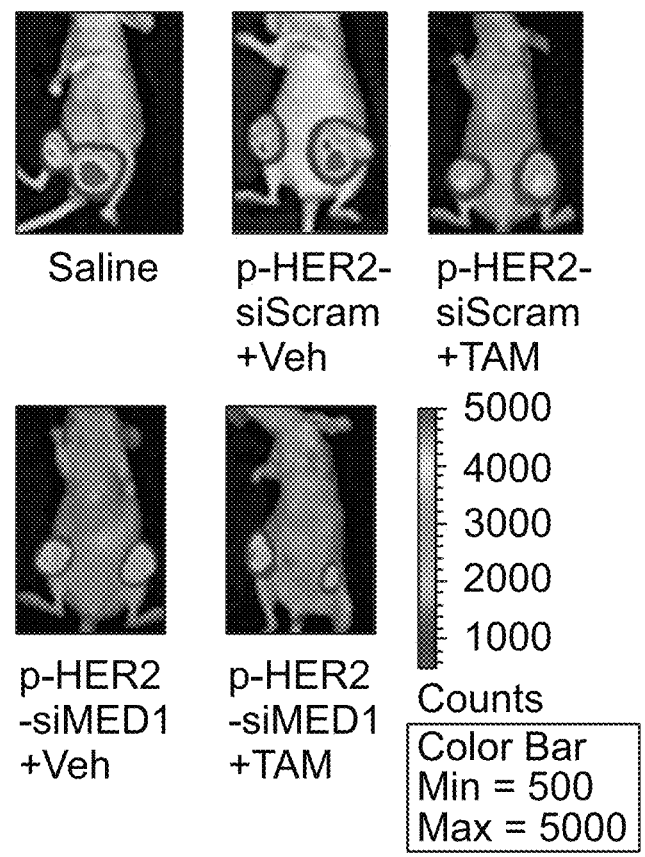
Figure 5C:
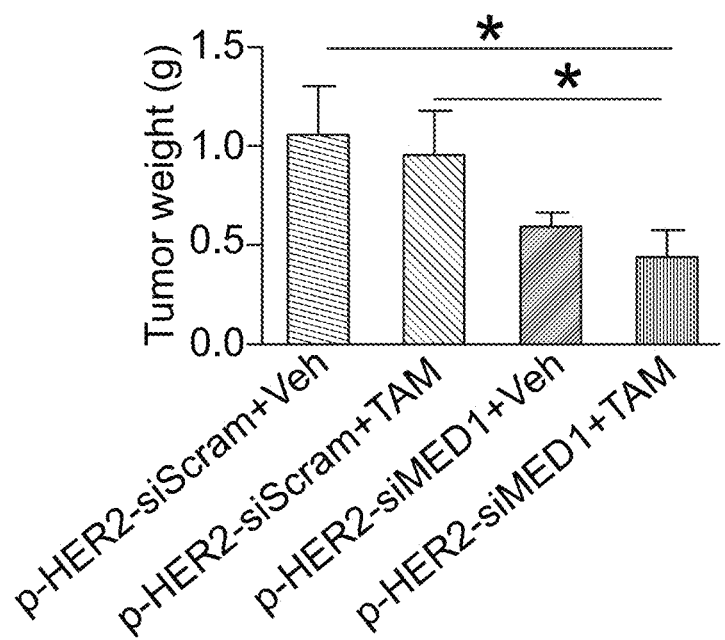
Figure 5D:
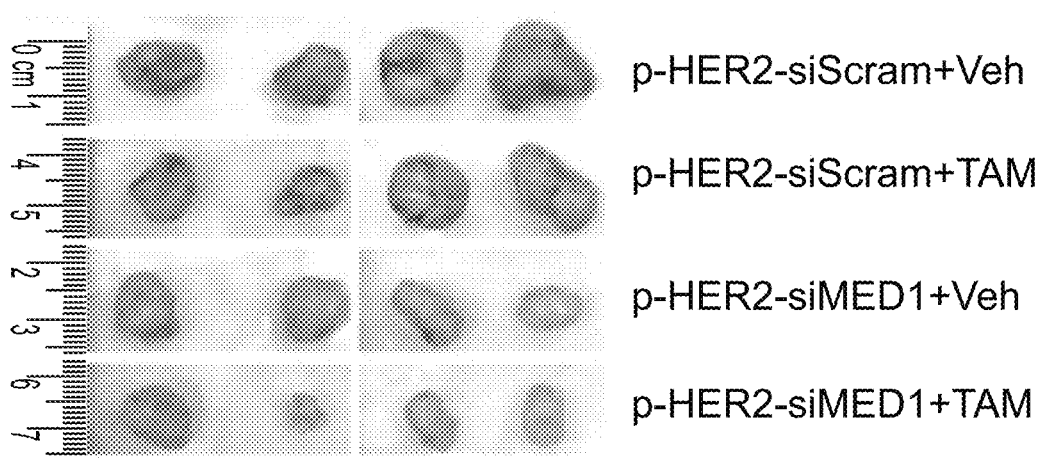
Figure 5E:
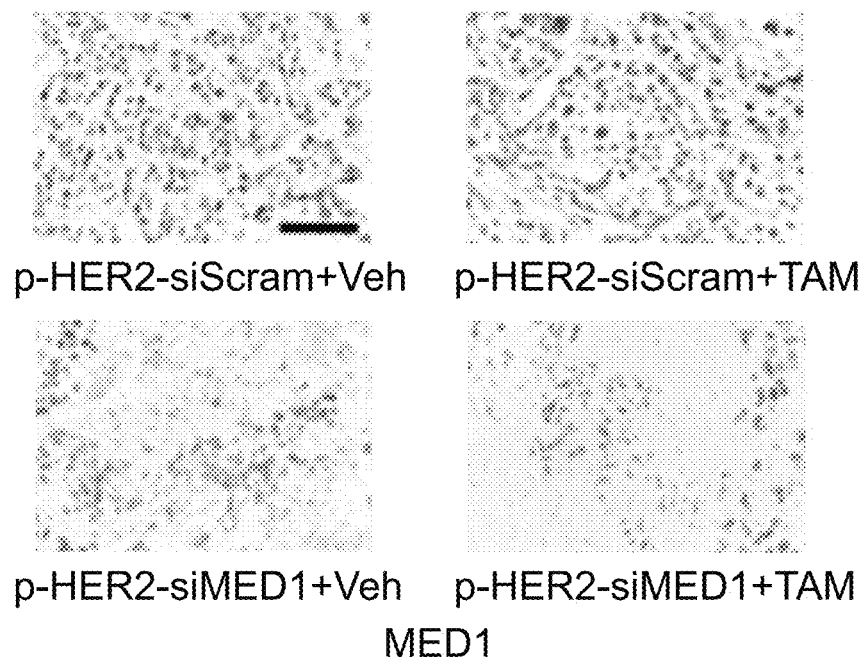
Figure 5F:
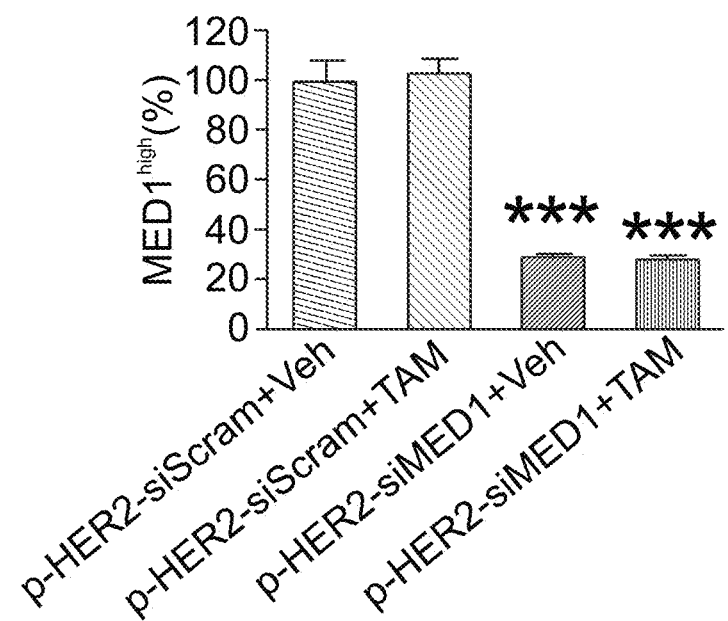
Figure 5G:
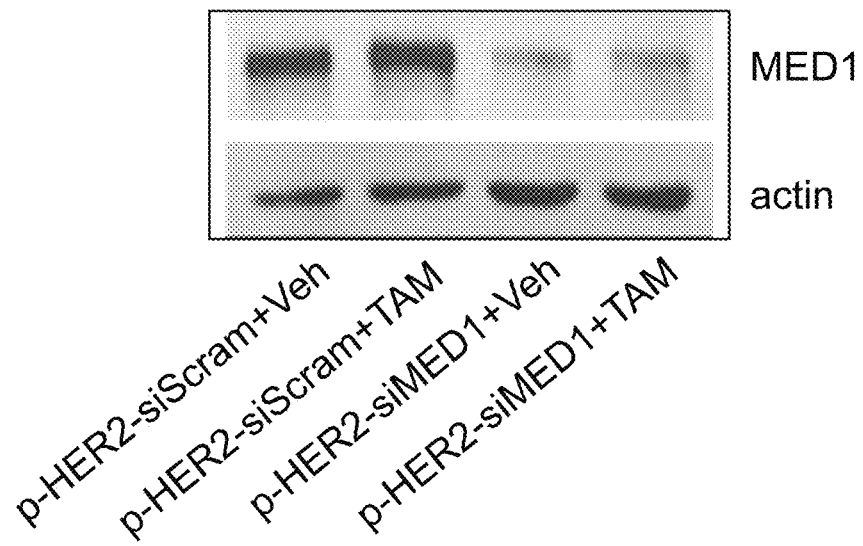
Figure 5H:
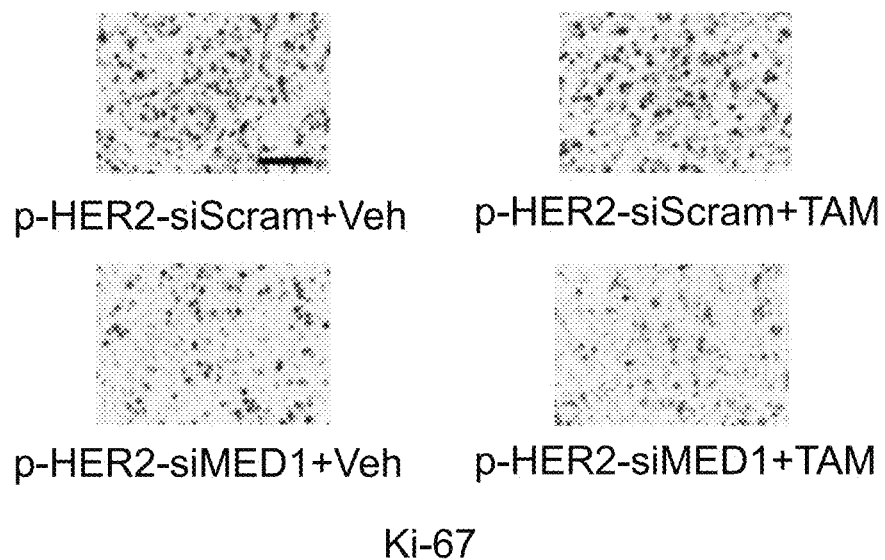
Figure 5I:
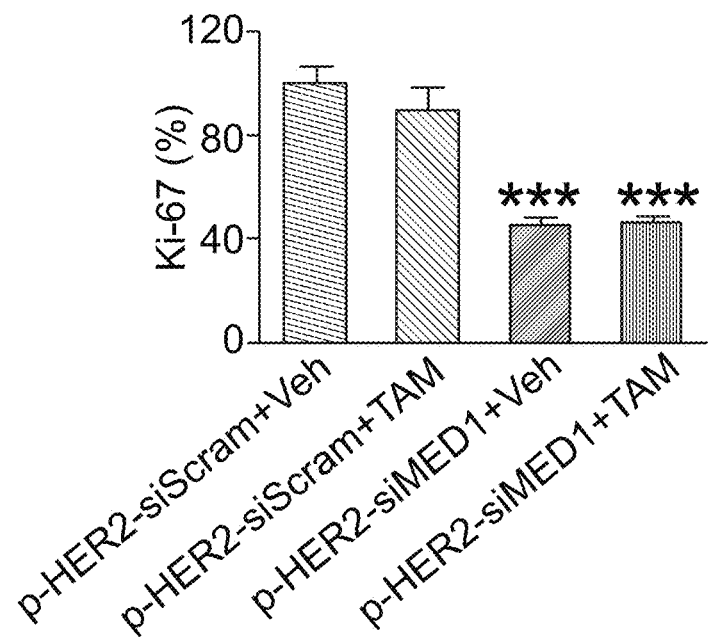
Figure 12A:
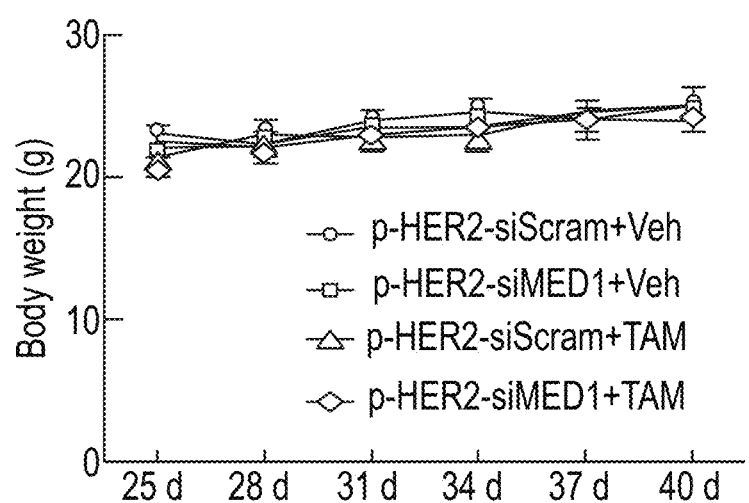
FIGS. 12A and 12B. Evidence that pRNA-HER2apt-siMED1 nanoparticles exhibit excellent biosafety.
Figure 12B:
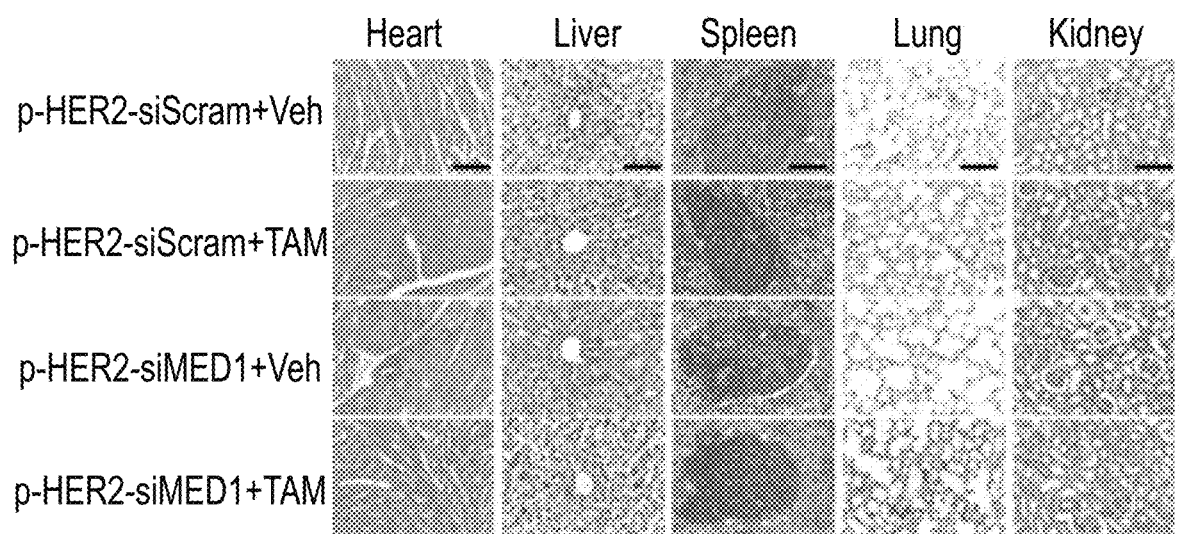

To further examine the potential therapeutic effects of pRNA-HER2apt-siMED1 nanoparticles in vivo, an orthotopic xenograft mouse model generated using luciferase-overexpressing BT474 cells was employed. After the tumor reached a size of ~100 mm³, the mice were randomly divided into 4 groups and systemically administrated with pRNA nanoparticles alone or in combination with tamoxifen. As shown in FIGS. 5A-D, pRNA-HER2apt-siMED1 nanoparticles alone significantly inhibited tumor growth and reduced tumor burden, whereas, tamoxifen treatment only weakly inhibited the growth of these tamoxifen resistant breast tumors as expected. More importantly, pRNA-HER2apt-siMED1 in combination with tamoxifen treatment further enhanced the inhibitory effect and almost completely suppressed tumor growth (FIGS. 5A-D). Immunochemistry staining and western blot analyses further confirmed that the expression of MED1 was significantly depleted in the pRNA-HER2apt-siMED1-treated groups (FIGS. 5E-G). Consistent with the suppressive effect on tumor growth, we found a dramatic reduction of Ki-67 expression in the tumor sections from pRNA-HER2apt-siMED1-treated groups (FIGS. 5H-I). Importantly, the pRNA nanoparticles exhibited great biosafety after systemic administration, as indicated by no significant reduction of mouse body weight during the entire treatment period (FIG. 12A). Moreover, the histopathology of major organs including heart, liver, spleen, lung and kidney was explored by H&E staining and there was no evidence of any apparent organ injury or disturbance in these tissues, further indicating excellent biosafety of pRNA-HER2apt-siMED1 nanoparticles (FIG. 12B).

Example 5

This example illustrates inhibition of breast cancer lung metastasis, stem cell formation and associated target gene expression by pRNA-HER2apt-siMED1 nanoparticles in vivo.

Figure 6A:
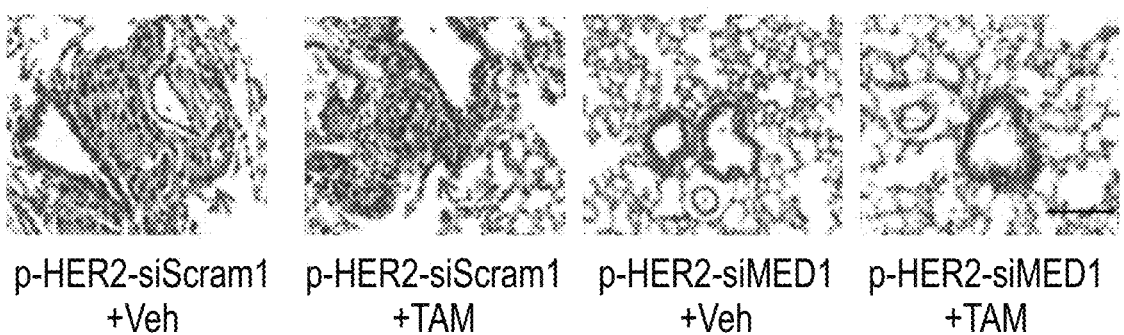
FIGS. 6A-6H. Evidence that pRNA-HER2apt-siMED1 in combination with tamoxifen greatly impaired breast cancer lung metastasis, stem cell formation and associated gene expression in vivo.
Figure 6B:
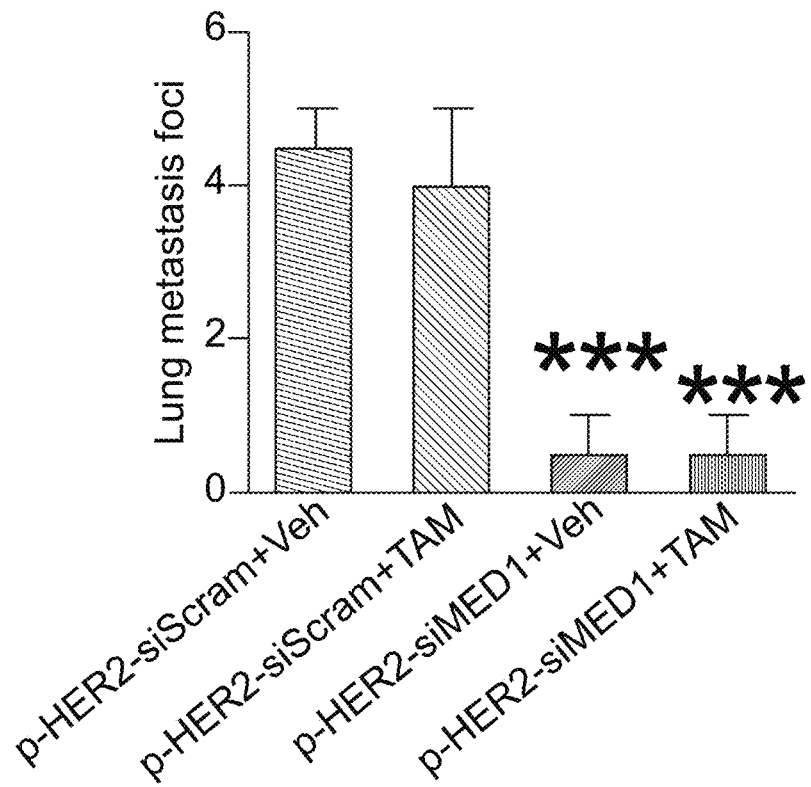
Figure 6C:
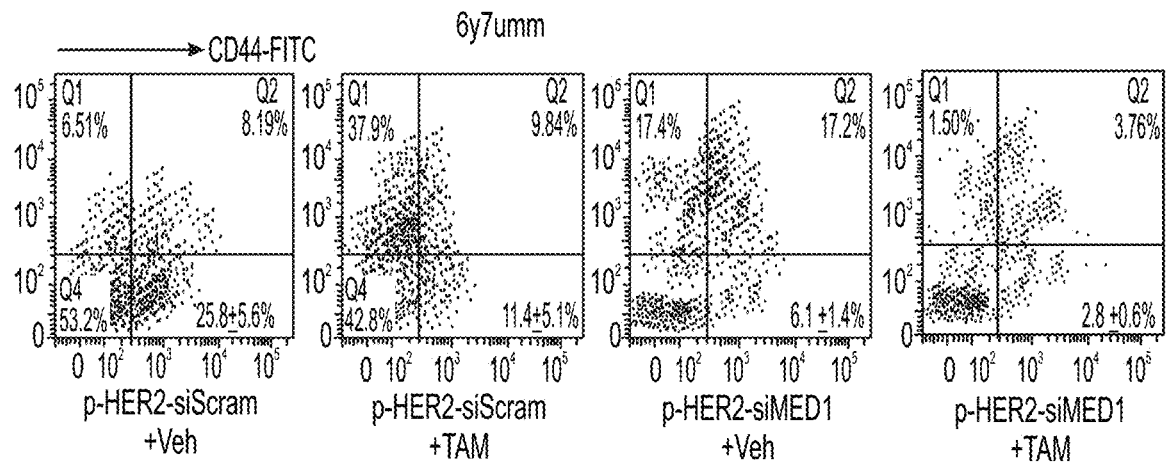
Figure 6D:
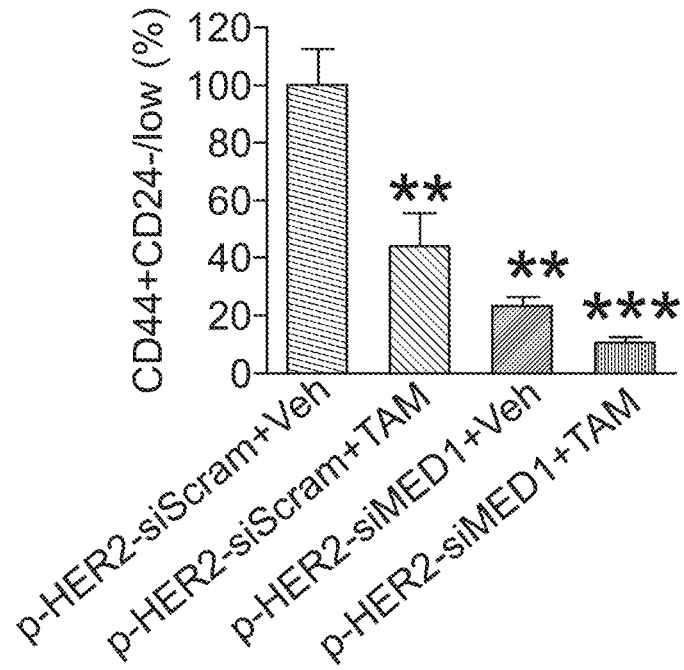
Figure 6E:
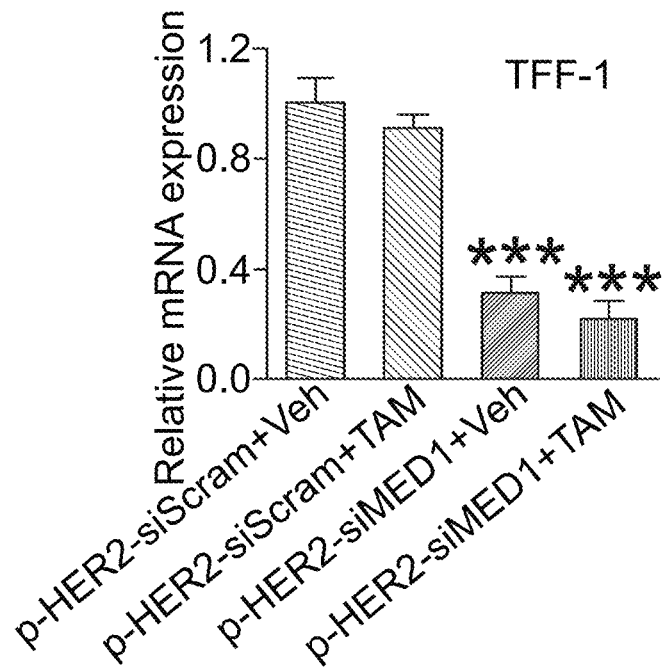
Figure 6F:
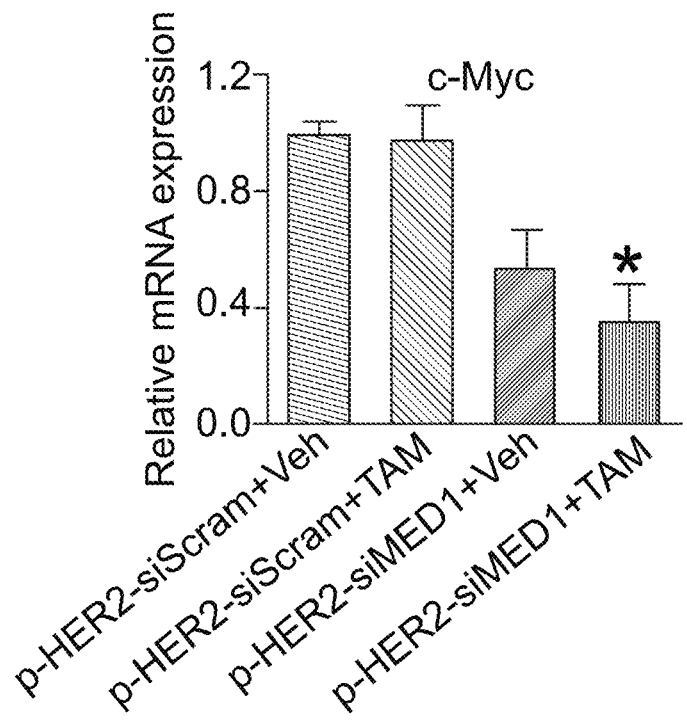
Figures 6G, 6H:
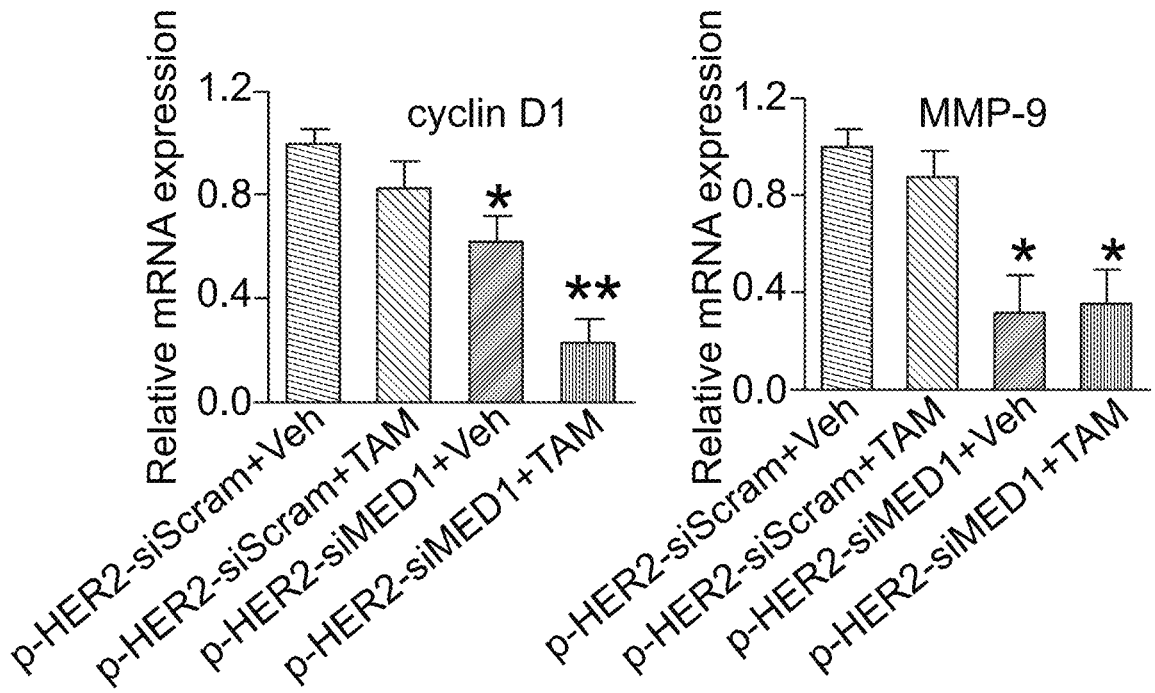

Since enhanced tumor metastasis and cancer stem cell formation are the major hallmarks of endocrine therapy resistance, tumor lung metastasis and cancer stem cell population in the tumor tissues after the therapeutic treatments was examined. H&E staining results indicated that there were multiple tumor lung metastasis foci in the scramble control or tamoxifen-treated groups (FIGS. 6A-B). However, treatments with pRNA-HER2apt-siMED1 nanoparticles alone or in combination with tamoxifen totally eradicated tumor lung metastasis. Further flow cytometric results revealed that pRNA-HER2apt-siMED1 nanoparticles significantly reduced the CD44$^+$CD24$^{-/low}$ cancer stem cells in the breast tumors. Impressively, when combined with tamoxifen, pRNA-HER2apt-siMED1 nanoparticles led to almost complete depletion of the CD44$^+$CD24$^{-/low}$ cancer stem cells in breast tumors (FIGS. 6C-D). To further understand the molecular mechanism underlying the anti-cancer effect of pRNA-HER2apt-siMED1 nanoparticles, expression levels of key ERα-associated genes involved in metastasis and cancer stem cell formation were examined. Consistent with above results, it was found that ERα target genes TFF-1, c-Myc, and cyclin D1 as well as MMP-9 were significantly down-regulated by pRNA-HER2apt-siMED1 treatment (FIGS. 6E-H). Importantly, the expression of these genes was further inhibited when the treatment of pRNA-HER2apt-siMED1 nanoparticles was combined with tamoxifen. Together, this data indicates that pRNA-HER2apt-siMED1 nanoparticles could overcome tamoxifen resistance of HER2-overexpressing breast cancer by inhibiting tumor growth, lung metastasis, cancer stem cells and associated gene expression.

The invention claimed is:

1. A pRNA nanoparticle functionalized for targeted delivery of Mediator Subunit 1 (MED1) silencing RNA (siRNA) to human cancer cells via human epidermal growth factor receptor 2 (HER2) receptors, the nanoparticle comprising: a three-way junction (3-WJ) pRNA, a HER2-targeting RNA aptamer, and two different MED 1 siRNAs, wherein each of the HER-2 targeting RNA aptamer and the MED1 siRNAs is annealed to a separate extending arm of the 3-WJ pRNA, wherein the pRNA nanoparticle is selected from the group consisting of:
   pRNA-HER2mini apt-MED1-siRNA (SEQ ID NO: 13),
   pRNA-HER2A1 apt-MED1-siRNA (SEQ ID NO: 14),
   pRNA-HER2B3 apt-MED1-siRNA (SEQ ID NO: 15),
   pRNA-HER2C3 apt-MED1-siRNA (SEQ ID NO: 16),
   pRNA-HER2D3 apt-MED1-siRNA (SEQ ID NO: 17), and
   pRNA-HER2E1 apt-MED1-siRNA (SEQ ID NO: 18).

2. The pRNA nanoparticle according to claim 1 comprising a 2'F-modification.

3. The pRNA nanoparticle according to claim 1 having a diameter of about 7 nm to about 11 nm as measured by DLS scattering.

4. The pRNA nanoparticle according to claim 1, wherein the human cancer cells comprise one or more of breast, uterine, ovarian, lung, stomach, bladder and salivary cancer cells.

5. The pRNA nanoparticle according to claim 1, wherein the nanoparticle comprises 2'F-modified 3-WJ pRNA-HER2B3 apt-MED1-siRNA (SEQ ID NO: 15).

6. A pharmaceutical composition formulated for local or systemic administration comprising:
   the pRNA nanoparticle according to claim 1; and
   a pharmaceutically acceptable vehicle, and, optionally, a pharmaceutically acceptable excipient.

7. The pharmaceutical composition according to claim 6, further comprising at least one anti-estrogenic agent.

8. The pharmaceutical composition according to claim 7, wherein the anti-estrogenic agent is selected from Tamoxifen, Toremifene, Fulvestrant, Raloxifene, lasofoxifene, Bazedoxifene, RAD-1901, an aromatase inhibitor (AI), and combinations thereof.

9. The pharmaceutical composition according to claim 8, wherein the AI is selected from Letrozole, Anastrozole, and Exemestane.

10. A method for selectively inhibiting expression of MED1 in HER2-overexpressing cells, the method comprising administering a composition according to claim 6 to the cells.

11. A method for treating a human suffering from a cancer selected from breast, uterine, ovarian, stomach, lung, bladder, and salivary cancer, the method comprising administering to the human a pharmaceutical composition comprising at least one pRNA nanoparticle comprising a three-way junction (3-WJ) pRNA, a HER2-targeting RNA aptamer, and two different MED 1 siRNAs, wherein each of the HER-2 targeting RNA aptamer and the MED1 siRNAs is annealed to a separate extending arm of the 3-WJ pRNA.

12. The method according to claim 11, wherein the HER2-targeting RNA aptamer is selected from MINI (SEQ ID NO: 7), A1 (SEQ ID NO: 8), B3 (SEQ ID NO: 9), C3 (SEQ ID NO: 10), D3 (SEQ ID NO: 11), and E1 (SEQ ID NO: 12).

13. The method according to claim 11, wherein the RNA aptamer is 2'F-modified and the pRNA nanoparticle is selected from pRNA-HER2mini apt-MED1-siRNA (SEQ ID NO: 13), pRNA-HER2A1 apt-MED1-siRNA (SEQ ID NO: 14), pRNA-HER2B3 apt-MED1-siRNA (SEQ ID NO: 15), pRNA-HER2C3 apt-MED1-siRNA (SEQ ID NO: 16), pRNA-HER2D3 apt-MED1-siRNA (SEQ ID NO: 17), and pRNA-HER2E1 apt-MED1-siRNA (SEQ ID NO: 18).

14. The method according to claim 11, wherein the pRNA nanoparticle comprises 2'F-modified 3-WJ pRNA-HER2B3 apt-MED1-siRNA (SEQ ID NO: 15).

15. The method according to claim 11, wherein the cancer comprises breast cancer.

16. The method according to claim 15, wherein the breast cancer is resistant to treatment with anti-estrogenic agents, said resistance being primary or acquired.

* * * * *

SEQUENCE LISTING

```
<160> NUMBER OF SEQ ID NOS: 18

<210> SEQ ID NO 1
<211> LENGTH: 59
<212> TYPE: RNA
<213> ORGANISM: Artificial Sequence
<220> FEATURE:
<223> OTHER INFORMATION: pRNA-HER2apt-siScram, p1

<400> SEQUENCE: 1
ggaucacgcu ucauauacaa aggaucaauc auggccaauc uuauuucgcc caugaccuu      59

<210> SEQ ID NO 2
<211> LENGTH: 131
<212> TYPE: RNA
<213> ORGANISM: Artificial Sequence
<220> FEATURE:
<223> OTHER INFORMATION: pRNA-HER2apt-siScram, p2

<400> SEQUENCE: 2
ggucaugggc gaaauaagaa aggccaugug uauguggggg gaggacgaug cggucugcug     60
ugcuugauau gccccagacg acucgccccc cacauacuuu guugauccaa uguauaugaa    120
gcgugauccu u                                                         131

<210> SEQ ID NO 3
<211> LENGTH: 59
<212> TYPE: RNA
<213> ORGANISM: Artificial Sequence
<220> FEATURE:
<223> OTHER INFORMATION: pRNA-HER2apt-siMED1, p1

<400> SEQUENCE: 3
ggacagugaa agugagucaa aggaucaauc auggccaaag auguuacuuu gagagccuu      59

<210> SEQ ID NO 4
<211> LENGTH: 131
<212> TYPE: RNA
<213> ORGANISM: Artificial Sequence
<220> FEATURE:
<223> OTHER INFORMATION: pRNA-HER2apt-siMED1, p2

<400> SEQUENCE: 4
ggcucucaaa guaacaucua aggccaugug uaugugggg gaggacgaug cggucugcug      60
ugcuugauau gccccagacg acucgccccc cacauacuuu guugauccaa ugacucacuu    120
ucacuguccu u                                                         131

<210> SEQ ID NO 5
<211> LENGTH: 59
<212> TYPE: RNA
<213> ORGANISM: Artificial Sequence
<220> FEATURE:
<223> OTHER INFORMATION: pRNA-HER2apt(mut)-siMED1, p1

<400> SEQUENCE: 5
ggacagugaa agugagucaa aggaucaauc auggccaaag auguuacuuu gagagccuu      59

<210> SEQ ID NO 6
<211> LENGTH: 131
<212> TYPE: RNA
<213> ORGANISM: Artificial Sequence
<220> FEATURE:
```

-continued

<223> OTHER INFORMATION: pRNA-HER2apt(mut)-siMED1, p2

<400> SEQUENCE: 6

```
ggcucucaaa guaacaucua aggccaugug uaugugggau gaggaguaug aagauaccug    60
uacuugauau gccccagacg acauucccc cacauacuuu guugauccaa ugacucacuu    120
ucacuguccu u                                                        131
```

<210> SEQ ID NO 7
<211> LENGTH: 34
<212> TYPE: RNA
<213> ORGANISM: Artificial Sequence
<220> FEATURE:
<223> OTHER INFORMATION: HER2 aptamer MINI

<400> SEQUENCE: 7

```
agccgcgagg ggagggauag gguagggcgc ggcu                               34
```

<210> SEQ ID NO 8
<211> LENGTH: 50
<212> TYPE: RNA
<213> ORGANISM: Artificial Sequence
<220> FEATURE:
<223> OTHER INFORMATION: HER2 aptamer A1

<400> SEQUENCE: 8

```
cggaggacga ugcgggacug uacggggcuc ugugcagacg acucgcccga              50
```

<210> SEQ ID NO 9
<211> LENGTH: 50
<212> TYPE: RNA
<213> ORGANISM: Artificial Sequence
<220> FEATURE:
<223> OTHER INFORMATION: HER2 aptamer B3

<400> SEQUENCE: 9

```
gggaggacga ugcggucugc ugugcuugau augccccaga cgacucgccc              50
```

<210> SEQ ID NO 10
<211> LENGTH: 50
<212> TYPE: RNA
<213> ORGANISM: Artificial Sequence
<220> FEATURE:
<223> OTHER INFORMATION: HER2 aptamer C3

<400> SEQUENCE: 10

```
gggaggacga ugcggcgaug cuuacgugca cgcgccagac gacucgcccg              50
```

<210> SEQ ID NO 11
<211> LENGTH: 48
<212> TYPE: RNA
<213> ORGANISM: Artificial Sequence
<220> FEATURE:
<223> OTHER INFORMATION: HER2 aptamer D3

<400> SEQUENCE: 11

```
gggaggacga ugcggucugu gugggaugug gccccagacg acucgccc                48
```

<210> SEQ ID NO 12
<211> LENGTH: 51
<212> TYPE: RNA
<213> ORGANISM: Artificial Sequence
<220> FEATURE:
<223> OTHER INFORMATION: HER2 aptamer E1

<400> SEQUENCE: 12

```
gggaggacga ugcgguccug ucgucuguuc gucccagac gacucgcccg a         51
```

<210> SEQ ID NO 13
<211> LENGTH: 171
<212> TYPE: RNA
<213> ORGANISM: Artificial Sequence
<220> FEATURE:
<223> OTHER INFORMATION: pRNA-HER2mini apt-MED1-siRNA

<400> SEQUENCE: 13

```
ggacagugaa agugagucaa aggaucaauc auggccaaag auguuacuuu gagagccggc    60
ucucaaagua acaucuaagg ccauguguau guggagccgc gagggagggg auaggguagg   120
gcgcggcucc cacauacuuu guugauccaa ugacucacuu ucacuguccu u            171
```

<210> SEQ ID NO 14
<211> LENGTH: 187
<212> TYPE: RNA
<213> ORGANISM: Artificial Sequence
<220> FEATURE:
<223> OTHER INFORMATION: pRNA-HER2A1 apt-MED1-siRNA

<400> SEQUENCE: 14

```
ggacagugaa agugagucaa aggaucaauc auggccaaag auguuacuuu gagagccggc    60
ucucaaagua acaucuaagg ccauguguau guggcggagg acgaugcggg acuuacgggg   120
gcucugugca gacgacucgc ccgacccaca uacuuuguug auccaaugac ucacuuucac   180
uguccuu                                                              187
```

<210> SEQ ID NO 15
<211> LENGTH: 188
<212> TYPE: RNA
<213> ORGANISM: Artificial Sequence
<220> FEATURE:
<223> OTHER INFORMATION: pRNA-HER2B3 apt-MED1-siRNA

<400> SEQUENCE: 15

```
ggacagugaa agugagucaa aggaucaauc auggccaaag auguuacuuu gagagccggc    60
ucucaaagua acaucuaagg ccauguguau guggggggag gacgaugcgg ucugcugugc   120
uugauaugcc ccagacgacu cgccccccac auacuuuguu gauccaauga cucacuuuca   180
cuguccuu                                                             188
```

<210> SEQ ID NO 16
<211> LENGTH: 187
<212> TYPE: RNA
<213> ORGANISM: Artificial Sequence
<220> FEATURE:
<223> OTHER INFORMATION: pRNA-HER2C3 apt-MED1-siRNA

<400> SEQUENCE: 16

```
ggacagugaa agugagucaa aggaucaauc auggccaaag auguuacuuu gagagccggc    60
ucucaaagua acaucuaagg ccauguguau gugggggagg acgaugcggc gaugcuuacg   120
ugcacgcgcc agacgacucg cccgcccaca uacuuuguug auccaaugac ucacuuucac   180
uguccuu                                                              187
```

<210> SEQ ID NO 17
<211> LENGTH: 185
<212> TYPE: RNA
<213> ORGANISM: Artificial Sequence
<220> FEATURE:

-continued

```
<223> OTHER INFORMATION: pRNA-HER2D3 apt-MED1-siRNA

<400> SEQUENCE: 17
ggacagugaa agugagucaa aggaucaauc auggccaaag auguuacuuu gagagccggc      60
ucucaaagua acaucuaagg ccauguguau guggggagg acgaugcggu cuguguggga     120
uguggcccca gacgacucgc cccccacaua cuuuguugau ccaaugacuc acuuucacug    180
uccuu                                                                185

<210> SEQ ID NO 18
<211> LENGTH: 188
<212> TYPE: RNA
<213> ORGANISM: Artificial Sequence
<220> FEATURE:
<223> OTHER INFORMATION: pRNA -HER2E1 apt-MED1-siRNA

<400> SEQUENCE: 18
ggacagugaa agugagucaa aggaucaauc auggccaaag auguuacuuu gagagccggc      60
ucucaaagua acaucuaagg ccauguguau guggggagg acgaugcggu ccugucgucu     120
guucgucccc agacgacucg cccgacccac auacuuuguu gauccaauga cucacuuuca    180
cuguccuu                                                             188
```